United States Patent
Kajihara et al.

(10) Patent No.: US 10,047,042 B2
(45) Date of Patent: Aug. 14, 2018

(54) METHOD FOR PRODUCING D-FORM OR L-FORM AMINO ACID DERIVATIVE HAVING THIOL GROUP

(71) Applicant: Glytech, Inc., Kyoto (JP)

(72) Inventors: Yasuhiro Kajihara, Osaka (JP); Yasuhito Morishita, Osaka (JP); Takefumi Murase, Kyoto (JP)

(73) Assignee: GLYTECH, INC., Kyoto (JP)

( * ) Notice: Subject to any disclaimer, the term of this patent is extended or adjusted under 35 U.S.C. 154(b) by 0 days.

(21) Appl. No.: 15/030,970

(22) PCT Filed: Oct. 22, 2014

(86) PCT No.: PCT/JP2014/078136
§ 371 (c)(1),
(2) Date: Apr. 21, 2016

(87) PCT Pub. No.: WO2015/064453
PCT Pub. Date: May 7, 2015

(65) Prior Publication Data
US 2016/0304449 A1    Oct. 20, 2016

(30) Foreign Application Priority Data

Nov. 1, 2013   (JP) .................. 2013-228790

(51) Int. Cl.
| | | |
|---|---|---|
| C12P 13/22 | (2006.01) | |
| C12P 13/02 | (2006.01) | |
| C12N 9/10 | (2006.01) | |
| C07C 319/28 | (2006.01) | |
| C07B 57/00 | (2006.01) | |
| C12P 41/00 | (2006.01) | |
| C07C 319/02 | (2006.01) | |
| C07H 21/04 | (2006.01) | |
| C12N 9/80 | (2006.01) | |

(52) U.S. Cl.
CPC ............ C07C 319/28 (2013.01); C07B 57/00 (2013.01); C07C 319/02 (2013.01); C12P 13/222 (2013.01); C12P 13/225 (2013.01); C12P 41/001 (2013.01); C07B 2200/07 (2013.01); C12N 9/80 (2013.01)

(58) Field of Classification Search
CPC ..... C12P 13/222; C12P 41/001; C12P 13/225; C12N 9/80; C07C 319/28
USPC .................... 435/195, 196, 227, 228, 231
See application file for complete search history.

(56) References Cited

U.S. PATENT DOCUMENTS

| | | |
|---|---|---|
| 4,024,175 A | 5/1977 | Satzinger et al. |
| 6,063,615 A | 5/2000 | Sturmer et al. |
| 6,197,762 B1 | 3/2001 | Garvey et al. |
| 9,704,319 B2 | 7/2017 | Desinor, Jr. |
| 2003/0236253 A1 | 12/2003 | Chizh et al. |

FOREIGN PATENT DOCUMENTS

WO    WO 03/029477 A1    4/2003

OTHER PUBLICATIONS

Davos et al., (Proteins: Structure, Function and Genetics, 2000, vol. 41: 98-107.*
Wristlock et al., (Quarterly Reviews of Biophysics 2003, vol. 36 (3): 307-340.*
Kwiatkowski et al., (Biochemistry 38:11643-11650, 1999.*
Kisselev L., (Structure, 2002, vol. 10: 8-9.*
Morishita, Y. et al. "Development of a concise synthetic strategy of s-mercapto amino acid derivatives", *Proceedings of 4th Asia Pacific International Peptide Symposium Document 3: 50th Japanese Peptide Symposium 2013*, Oct. 10, 2013, pp. 113.
Morishita, Y. et al., "Racemic synthesis of amino acid derivatives having thiol at the be-ta position", Abstract of the 94th Annual Meeting of CSJ, Mar. 12, 2014, p. 1471.
Wong, et al., "Synthetic cysteine surrogates used in native chemical ligation", Molecular BioSystems, May 7, 2013, vol. 9, No. 5, pp. 826-883.
Bornscheuer, et al., "Hydrolases in Organic Synthesis", *Regio- and Stereoselective Biotransformations*, 2nd Edition, 2006, 7 pages.
Fogassy, Elmer et al., "Optical resolution methods", *Organic & Biomolecular Chemistry*, (2006) pp. 3011-3030.
Translation of Written Opinion and International Search Report corresponding to International Patent Application No. PCT/JP2014/078136, dated Jan. 27, 2015, 7 pages.
Dong-Mi, Li. et al., "Highly Enationaselective Recognition of a Wide Range of Carboxylic Acids Based on Enantioselectively Aggregation-Induced Emission", *Chemical Communications—CHEMCOM.*, vol. 47, No. 36, Jan. 1, 2011, p. 10139, Abstract.

* cited by examiner

*Primary Examiner* — Robert B Mondesi
*Assistant Examiner* — Mohammad Y Meah
(74) *Attorney, Agent, or Firm* — Myers Bigel, P.A.

(57) ABSTRACT

The object of the present invention is to provide a method of efficiently manufacturing an optically active D- and/or L-form amino acid possessing a thiol group in the side chain by a simple method. The present invention provides a method of manufacturing an amino acid derivative possessing a thiol group in the side chain, characterized in manufacturing an intermediate composition comprising D- and L-forms of an amino acid derivative possessing a thiol group at the β-position, reacting a hydrolase selective for D- or L-amino acids, and separating the hydrolyzed D- or L-amino acid derivative, as well as an intermediate thereof.

14 Claims, 1 Drawing Sheet

[Fig. 1]
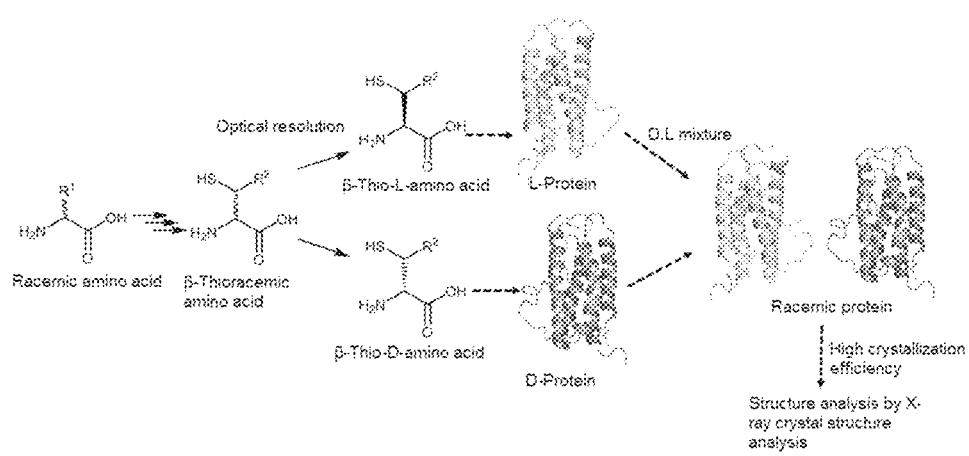
[Fig. 2]
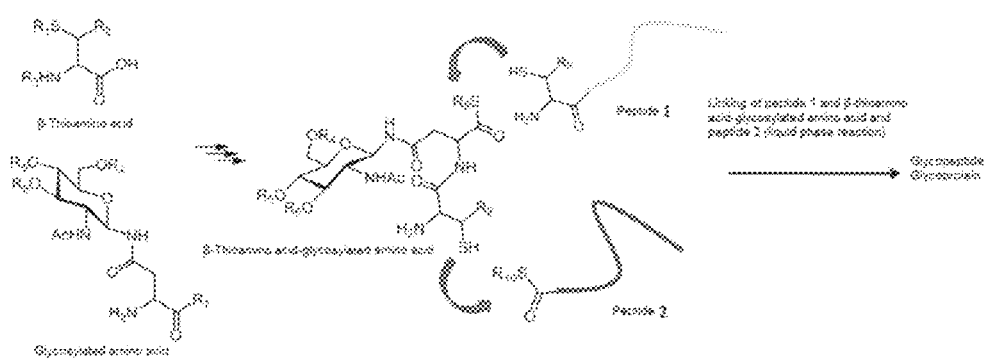

METHOD FOR PRODUCING D-FORM OR L-FORM AMINO ACID DERIVATIVE HAVING THIOL GROUP

STATEMENT OF PRIORITY

This application is a 35 U.S.C. § 371 national phase application of International Application Ser. No. PCT/JP2014/078136, filed Oct. 22, 2014, which claims the benefit, under 35 U.S.C. § 119 (a) of Japanese Patent Application No. 2013-228790, filed Nov. 1, 2013, the entire contents of each of which are incorporated by reference herein.

TECHNICAL FIELD

The present invention relates to a method of manufacturing a D- or L-form amino acid derivative possessing a thiol group in the side chain. The present invention also relates to an intermediate employed in the method of manufacturing a D- or L-form amino acid derivative possessing a thiol group in the side chain.

BACKGROUND ART

Research and development of biopharmaceuticals have progressed in recent years, and there are increasing examples of synthesizing peptides and proteins to analyze structure or function, or employing peptides and proteins as medicines. Peptides and proteins are composed of amino acids, and because in α-amino acids that configure proteins the α carbon atom is an asymmetric atom except when the side chain substituent is a hydrogen atom, enantiomers referred to as D- and L-forms exist. Since peptides and proteins that exist in vivo are configured by L-amino acids, optically active L-amino acids are required as the raw material in order to synthesize peptides and proteins that exist in vivo. Moreover, X-ray crystal structure analysis employing racemic proteins are recently gathering attention in protein structure analysis with expectations to increase the crystallization efficiency of proteins. Here, a racemic protein is a protein that is an equal mixture of a protein consisting of only D-amino acids and a protein consisting of only L-amino acids. Analysis of protein structure is an important knowledge in understanding protein function. Demands to synthesize both D- and L-proteins in order to perform structural analysis by crystallization of such racemic proteins are increasing. In order to manufacture such D- and/or L-proteins and stably supply them, it is necessary to efficiently manufacture large amounts of each of optically active D- and L-amino acids as the raw material. In particular, since D-proteins do not exist in nature and can only be synthesized by chemical synthesis, industrial production of D-amino acids to be used as the raw material is essential.

Moreover, when synthesizing a protein as a large molecule, because the length of a peptide that can be manufactured is restricted in the method of manufacturing a peptide by solid phase synthesis etc., the manufactured peptides must be linked. A method referred to as NCL (Native Chemical Ligation) is employed as the peptide linking method. In NCL, a peptide comprising an amino acid possessing a thiol group in the side chain at the N-terminal is linked with the C-terminal of another peptide by utilizing the reactivity of the thiol group. Accordingly, in NCL, protein synthesis is designed mainly with cysteine, which is an amino acid possessing a thiol group in the side chain, as the linking site. For example, a method of having alanine etc. as the linking site by carrying out the linking reaction with a thiol group and then structurally changing it into other amino acids has also been devised. However, amino acids that can be the linking site are still very limited, and this has been the constraint in protein synthesis.

Accordingly, in the manufacture of a D- or L-protein as a large molecule, optically active D- or L-amino acids having a thiol group introduced into the side chain must be manufactured in order to manufacture an amino acid that may be the linking site for NCL. However, although a method of introducing a thiol group into the side chain with D- or L-amino acids as the raw material and via numerous complex steps so that isomerization does not occur has been attempted as the method of manufacturing such amino acids, it is very difficult to manufacture the amino acid of interest with good yield amount and rate by such a method. Reports related to for example a method of employing an enzyme that has stereoselectivity as the method of manufacturing an optically active amino acid also exist (see Patent Literatures 1 and 2). However, there is no particular description in these regarding for example the manufacture of an amino acid possessing a desired substituent such as a thiol group in the side chain. Moreover, since enzymes have substrate specificity, it cannot be said that such enzymes are also effective for an amino acid derivative possessing a bulky substituent such as a protected thiol group at the β-position. Further, in the manufacture of a D- or L-protein as a large molecule, an optically active β-thioamino acid derivative that may be employed as the linking site for NCL has thus far not been manufactured in an aspect that will enable industrial production of D- or L-proteins.

CITATION LIST

[Patent Literature 1] Japanese Published Unexamined Patent Application Publication No. H6-125786
[Patent Literature 2] Japanese Published Unexamined Patent Application Publication No. H11-69992

SUMMARY OF THE INVENTION

Problems to be Solved by the Invention

The object of the present invention is to provide a method of efficiently manufacturing an optically active D- and/or L-form amino acid possessing a thiol group in the side chain by a simple method. In particular, the present inventors set the objective to efficiently manufacture various natural or non-natural D- or L-amino acids possessing a thiol group in the side chain in order to increase the variation of amino acids that may be the linking site for NCL.

Means for Solving the Problems

The present inventors carried out extensive investigations in order to solve the above problems. According to the conventional method that uses optically active D- or L-amino acids as the raw material, controlling of stereoisomerism of asymmetric carbon atoms was very difficult. Accordingly, the present inventors surprisingly found that an optically active amino acid derivative possessing a thiol group in the side chain can be manufactured at high yield with a simple method having fewer steps than the conventional by choosing to manufacture the amino acid derivative possessing a thiol group as an intermediate composition with mixed stereoisomers, and then separating D- and L-forms for the α carbon atom with an enzyme. In other words, the present inventors focused on the fact that it is possible to employ a method of removing the thiol group employed in the peptide linking reaction after the linking reaction in the NCL method. The present inventors thought that an amino acid derivative possessing a thiol group at the β-position (a β-thioamino acid derivative) can, without controlling stereoisomerism for α and β carbon atoms, be ultimately purified and obtained as the optically active form for the α carbon atom and employed as the linking site for NCL. In other words, because the D- or L-form of a β-thioamino acid derivative in which α and β carbon atoms are asymmetric atoms will become an optically active D- or L-form for the α carbon atom in which only the α carbon atom is the asymmetric carbon atom by removing the thiol group after the NCL reaction, it can be favorably employed as the amino acid employed for the NCL linking site.

Further, the present inventors carried out extensive investigations for a method of manufacturing an amino acid derivative composition of mixed stereoisomers as an intermediate in order to manufacture an optically active derivative having a thiol group introduced into various natural or non-natural amino acids. As a result, the present inventors found that by employing an aromatic amino acid or glycine as the raw material, a non-natural amino acid having a thiol group introduced into the side chain of various amino acids including natural amino acids can be easily manufactured at a high yield as a D- or L-form amino acid.

In other words, the present invention provides a method of manufacturing a non-natural D- or L-amino acid derivative possessing a protected or non-protected thiol group at the β-position. This manufacturing method is characterized in manufacturing an amino acid derivative possessing a protected or non-protected thiol group at the β-position comprising D- and L-forms, reacting the amino acid derivative obtained with a hydrolase selective for either one of D- or L-amino acids, and subsequently separating the hydrolyzed D- or L-amino acid derivative.

Moreover, one embodiment of the present invention provides a method of manufacturing a non-natural D- or L-amino acid derivative possessing a protected or non-protected thiol group at the β-position, characterized in that it comprises the following steps of:

(I) carrying out the following reactions on an amino acid derivative to manufacture an amino acid derivative possessing a protected or non-protected thiol group at the β-position comprising D- and L-forms:

(A) a reaction of introducing a protected or non-protected thiol group at the β carbon atom of said amino acid derivative, and (B) a reaction of converting the amino group or carboxyl group bound to the α carbon atom of said amino acid derivative into a substituent to be the substrate for a hydrolase selective for D- or L-amino acids, and (II) reacting the amino acid derivative obtained in (I) with a hydrolase selective for either one of D- or L-amino acids, and subsequently separating the hydrolyzed D- or L-amino acid derivative.

Moreover, one embodiment of the present invention provides a method of manufacturing a non-natural D- or L-amino acid derivative possessing a protected or non-protected thiol group and substituent $R^1$ at the β-position [wherein $R^1$ refers to the substituent moiety bound to the β carbon atom among side chain substituents that configure amino acids (except when it is a hydrogen atom)].

Moreover, one embodiment of the present invention is characterized in that it is said "method of manufacturing a non-natural D- or L-amino acid derivative possessing a protected or non-protected thiol group and substituent $R^1$ at the β-position," wherein said step (I) comprises a step of manufacturing an amino acid derivative possessing substituent $R^1$ and a leaving group L on the β carbon atom as step (P) before said reaction (A), and said reaction (A) is carried out simultaneously with a reaction of detaching said leaving group L from the β carbon atom of the amino acid derivative.

Moreover, one embodiment of the present invention is characterized in that said substituent $R^1$ is an aromatic substituent, and said step (P) comprises a step of introducing a leaving group L at the β carbon atom of an amino acid derivative possessing substituent $R^1$ on the β carbon atom as step (P-1).

Moreover, one embodiment of the present invention is characterized in that said step (P) comprises a step of reacting glycine with an aldehyde compound represented by $R^1CHO$ as step (P-2).

Moreover, one embodiment of the present invention is characterized in that said step (B) is a reaction of converting the amino group bound to the α carbon atom of said amino acid derivative into an acylamino group, and the hydrolase selective for D- or L-amino acids in said step (II) is a D- or L-aminoacylase.

Moreover, one embodiment of the present invention is characterized in that the step of separating the hydrolyzed D- or L-amino acid derivative in said step (II) comprises a step of introducing a lipophilic protecting group into the hydrolyzed D- or L-amino acid derivative, and is a step of utilizing the difference in hydrophobicity produced by the presence or absence of the lipophilic protecting group to separate the D- or L-amino acid derivative having the lipophilic protecting group introduced.

Moreover, one embodiment of the present invention is characterized in that it is a method of manufacturing a non-natural D-amino acid derivative possessing a protected or non-protected thiol group at the β-position, wherein in said step (II) a hydrolase selective for D-amino acids is employed, and subsequently the hydrolyzed D-amino acid derivative is separated.

Moreover, one embodiment of the present invention is characterized in that it is a method of manufacturing a non-natural L-amino acid derivative possessing a protected or non-protected thiol group at the β-position, wherein in said step (II) a hydrolase selective for L-amino acids is employed, and subsequently the hydrolyzed L-amino acid derivative is separated.

Moreover, one embodiment of the present invention is characterized in that the thiol group introduced in said step (A) is a thiol group protected by a protecting group selected from a PMB (para-methoxybenzyl) group, an Acm (acetamidomethyl) group, a benzyl group, a Trt (trityl) group, a disulfide group, and a t-butyl group.

Moreover, one embodiment of the present invention provides a method of manufacturing optically resolved non-natural D- and L-amino acid derivatives possessing a protected or non-protected thiol group at the β-position, comprising the following steps of:

(I) carrying out the following reactions on an amino acid derivative to manufacture an amino acid derivative possessing a protected or non-protected thiol group at the β-position comprising D- and L-forms:

(A) a reaction of introducing a protected or non-protected thiol group at the β carbon atom of said amino acid derivative, and (B) a reaction of converting the amino group or carboxyl group bound to the α carbon atom of said amino acid derivative into a substituent to be the substrate for a hydrolase selective for D- or L-amino acids, (II) reacting the amino acid derivative obtained in (I) with a hydrolase selective for D-amino acids, and subsequently separating the hydrolyzed D-amino acid derivative, and (III) hydrolyzing the L-amino acid derivative that was not hydrolyzed in (II), and subsequently obtaining the hydrolyzed L-amino acid derivative.

Moreover, one embodiment of the present invention provides a method of manufacturing optically resolved non-natural D- and L-amino acid derivatives possessing a protected or non-protected thiol group at the β-position, comprising the following steps of:

(I) carrying out the following reactions on an amino acid derivative to manufacture an amino acid derivative possessing a protected or non-protected thiol group at the β-position comprising D- and L-forms:

(A) a reaction of introducing a protected or non-protected thiol group at the β carbon atom of said amino acid derivative, and (B) a reaction of converting the amino group or carboxyl group bound to the α carbon atom of said amino acid derivative into a substituent to be the substrate for a hydrolase selective for D- or L-amino acids, (II) reacting the amino acid derivative obtained in (I) with a hydrolase selective for L-amino acids, and subsequently separating the hydrolyzed L-amino acid derivative, and (III) hydrolyzing the D-amino acid derivative that was not hydrolyzed in (II), and subsequently obtaining the hydrolyzed D-amino acid derivative.

Moreover, one embodiment of the present invention provides a method of manufacturing optically resolved non-natural D- and L-amino acid derivatives possessing a protected or non-protected thiol group at the β-position, wherein said step (B) is a reaction of converting the amino group bound to the α carbon atom of said amino acid derivative into an acylamino group, "the amino acid derivative obtained in (I)" described in step (II) is a composition comprising D- and L-forms for the α carbon atom represented by the following formula:

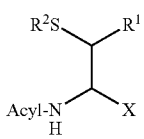

[Chemical Formula 1]

[wherein $R^2$ represents a hydrogen atom or a protecting group for the thiol group, X represents a protected or non-protected carboxyl group, Acyl indicates an acyl group, and $R^1$ indicates the substituent moiety bound to the β carbon atom among side chain substituents that configure amino acids (except when it is a hydrogen atom)], and the hydrolase selective for D- or L-amino acids in said step (II) is a D- or L-aminoacylase.

As another embodiment, the present invention also provides a composition comprising D- and L-forms for the α carbon atom of the amino acid derivative represented by the following formula:

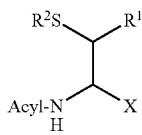

[Chemical Formula 2]

[wherein $R^2$ represents a hydrogen atom or a protecting group for the thiol group, X represents a protected or non-protected carboxyl group, Acyl indicates an acyl group, and $R^1$ indicates the substituent moiety bound to the β carbon atom among side chain substituents that configure natural amino acids (except when it is a hydrogen atom)]. Moreover, such an amino acid derivative may be a salt of a compound represented by the above formula.

Moreover, one embodiment of the present invention is characterized in that in the composition comprising D- and L-forms for the α carbon atom of the amino acid derivative represented by the above formula, said substituent $R^1$ is the substituent moiety bound to the β carbon atom of an amino acid selected from the group consisting of Arg, Asn, Asp, Glu, Gln, His, Leu, Lys, Met, Phe, Trp, and Tyr (provided that it is not a hydrogen atom).

Moreover, one embodiment of the present invention is characterized in that in the composition comprising D- and L-forms for the α carbon atom of the amino acid derivative represented by the above formula, said substituent $R^2$ is a protecting group for the thiol group.

Moreover, one embodiment of the present invention is characterized in that in the composition comprising D- and L-forms for the α carbon atom of the amino acid derivative represented by the above formula, said substituent X is COOH.

Moreover, one embodiment of the present invention is characterized in that in the composition comprising D- and L-forms for the α carbon atom of the amino acid derivative represented by the above formula, said substituent $R^1$ is the substituent moiety bound to the β carbon atom of an amino acid selected from the group consisting of Arg, Asn, Asp, Glu, Gln, His, Leu, Lys, Met, Phe, Trp, and Tyr (provided that it is not a hydrogen atom), said substituent $R^2$ is a protecting group for the thiol group, and said substituent X is COOH.

Moreover, one embodiment of the present invention is characterized in that the composition comprising D- and L-forms for the α carbon atom of the amino acid derivative represented by the above formula is an equal mixture of said D- and L-forms.

Moreover, one embodiment of the present invention provides a method of manufacturing a non-natural D- or L-amino acid derivative possessing a protected or non-protected thiol group and substituent $R^1$ at the β-position [wherein $R^1$ refers to an aromatic substituent], comprising the following steps of:

(I) carrying out the following steps on an amino acid derivative to manufacture an amino acid derivative possessing a protected or non-protected thiol group at the β-position comprising D- and L-forms:

(P-1) introducing a leaving group L into said β carbon atom of an amino acid derivative possessing substituent $R^1$ on the β carbon atom to manufacture an amino acid derivative possessing substituent $R^1$ and a leaving group L on the β carbon atom.

(A) detaching said leaving group L from the β carbon atom of said amino acid derivative, and introducing a protected or non-protected thiol group into said β carbon atom, and (B) converting the amino group or carboxyl group bound to the α carbon atom of said amino acid derivative into a substituent to be the substrate for a hydrolase selective for D- or L-amino acids.
and (II) reacting the amino acid derivative obtained in (I) with a hydrolase selective for D- or L-amino acids, and subsequently separating the hydrolyzed D- or L-amino acid derivative.

Moreover, one embodiment of the present invention provides a method of manufacturing a non-natural D- or L-amino acid derivative possessing a protected or non-protected thiol group and substituent $R^1$ at the β-position [wherein $R^1$ refers to the substituent moiety bound to the β carbon atom among side chain substituents that configure amino acids (except when it is a hydrogen atom)], comprising the following steps of:

(I) carrying out the following steps on an amino acid derivative to manufacture an amino acid derivative possessing a protected or non-protected thiol group at the β-position comprising D- and L-forms:

(P-2) reacting glycine with an aldehyde compound represented by $R^1CHO$ to manufacture an amino acid derivative possessing substituent $R^1$ and a leaving group L on the β carbon atom, (A) detaching said leaving group L from the β carbon atom of said amino acid derivative, and introducing a protected or non-protected thiol group into said β carbon atom, and (B) converting the amino group or carboxyl group bound to the α carbon atom of said amino acid derivative into a substituent to be the substrate for a hydrolase selective for D- or L-amino acids,
and (II) reacting the amino acid derivative obtained in (I) with a hydrolase selective for D- or L-amino acids, and subsequently separating the hydrolyzed D- or L-amino acid derivative.

Moreover, one embodiment of the present invention is a method of manufacturing a non-natural D- or L-amino acid derivative possessing a protected or non-protected thiol group at the β-position, characterized in that an amino acid derivative comprising D- and L-forms for the α carbon atom or an amino acid derivative in which the α carbon atom is not an asymmetric carbon atom is employed as the raw material.

Moreover, one embodiment of the present invention is a method of manufacturing a non-natural D- or L-amino acid derivative possessing a protected or non-protected thiol group at the β-position, characterized in that an amino acid derivative as an equal mixture of D- and L-forms for the α carbon atom or an amino acid derivative in which the α carbon atom is not an asymmetric carbon atom is employed as the raw material.

Those skilled in the art shall recognize that an invention of any combination of one or more characteristics of the present invention described above is encompassed in the scope of the present invention.

EFFECTS OF THE INVENTION

According to the manufacturing method of the present invention, a non-natural amino acid possessing a thiol group in the side chain can be manufactured as a D- or L-form amino acid by a simpler method and at a higher yield compared to the conventional method that uses optically active amino acids as the raw material. In other words, according to the conventional manufacturing method that uses D- or L-form amino acids as the raw material, reactions employing a heating condition or a strong basic or strong acidic conditions could not be employed so as not to produce stereoisomerization for the α asymmetric carbon atom. In contrast, according to the manufacturing method of the present invention, an easier manufacturing step with superior reaction efficiency can be employed by employing these extreme conditions in the step of manufacturing the desired amino acid comprising the introduction of a thiol group.

Moreover, according to the manufacturing method of the present invention, a non-natural amino acid having a thiol group introduced into the side chain of various amino acids including natural amino acids can be manufactured easily and at a high yield as a D- or L-form amino acid.

By employing the amino acid derivative obtained by the manufacturing method of the present invention, various natural and non-natural amino acids other than cysteine could be employed as the linking site in the peptide linking method. In other words, the manufacturing method of the present invention broadens the application potential of the peptide linking method in protein synthesis and has high utility value in that there is no need to change the amino acid sequence for peptide linking in protein synthesis, and that protein synthesis could be designed with various amino acids in the amino acid sequence as the linking site.

Moreover, according to the manufacturing method of the present invention, because D- and L-form derivatives of the amino acid of interest are simultaneously synthesized without discriminating them as isomers, it is possible as one aspect of the present invention to separate D- and L-forms of the amino acid derivative of interest, and further to separately and simultaneously obtain both D- and L-forms as optically active forms. Such a method has high utility value as a method of providing a raw material that responds to the need of synthesizing both D- and L-form proteins.

According to the manufacturing method of the present invention, β-thioamino acids corresponding to most amino acid residues can be synthesized. As described above, the peptide linking method utilizing the NCL method has a constraint of being very limited in the amino acids that can be used as the linking site, but the restriction of peptide linking site in the NCL method is resolved by employing a β-thioamino acid of the manufacturing method of the present invention. This enables significant saving in the consumption of valuable amino acids in chemical synthesis of a polypeptide (or protein).

For example, when the valuable amino acid is a glycosylated amino acid, an excessive amount of glycosylated amino acid was consumed as the raw material in the conventional glycopeptide synthesis because the glycosylated amino acid was utilized in peptide solid phase synthesis. However, as described above, according to the manufacturing method of the present invention, since β-thioamino acid derivatives corresponding to most amino acid residues can be synthesized, a short-chain peptide of about a few residues that comprises a glycosylated amino acid and possesses a β-thioamino acid at the N-terminal and an activating group such as a thioester at the C-terminal can be synthesized and employed in a peptide linking reaction by the NCL method etc. (liquid phase reaction). In other words, the peptide could be efficiently elongated towards the N- and C-terminal sides with the valuable glycosylated amino acid in the center. This enabled significant saving in the consumption of valuable glycosylated amino acids or modified amino acids compared to the conventional solid phase synthesis method. For example, the schematic diagram of the reaction when the valuable amino acid is an amino acid possessing a sugar chain and the short-chain peptide is a two-amino acid unit composed of a β-thioamino acid and a glycosylated Asn is shown in FIG. 2.

BRIEF DESCRIPTION OF THE DRAWINGS

FIG. 1 shows the schematic diagram of one aspect of the manufacturing method of the present invention.

FIG. 2 shows the schematic diagram of an application example of a β-thioamino acid manufactured by one aspect of the manufacturing method of the present invention.

DESCRIPTION OF EMBODIMENTS

An "amino acid" is generally referred to as an organic compound possessing both amino group and carboxyl group. The carbon atom to which the carboxyl group is bound to is referred to as the α carbon atom, and when carbon atoms are linked to the α carbon atom, they are referred to as β and γ carbon atoms in order from the carbon atom adjacent to the α carbon atom. The α carbon atom is also referred to as the α-position carbon atom, or simply as the α-position in order to show the substituent binding position. This also applies to the β carbon atom etc.

An "amino acid" as used herein is employed in its broadest meaning, and comprises not only natural amino acids such as serine (Ser), asparagine (Asn), valine (Val), leucine (Leu), isoleucine (Ile), alanine (Ala), tyrosine (Tyr), glycine (Gly), lysine (Lys), arginine (Arg), histidine (His), aspartic acid (Asp), glutamic acid (Glu), glutamine (Gln), threonine (Thr), cysteine (Cys), methionine (Met), phenylalanine (Phe), tryptophan (Trp), and proline (Pro), but non-natural amino acids such as amino acid variants and derivatives. Those skilled in the art shall recognize in light of this broad definition that examples of an amino acid used herein include L-amino acids; D-amino acids; chemically modified amino acids such as amino acid variants and derivatives; amino acids that are not materials configuring proteins in vivo such as norleucine, β-alanine, and ornithine; and chemically synthesized compounds having properties of amino acids well-known to those skilled in the art.

The amino acid manufactured as the compound of interest in the manufacturing method of the present invention is not particularly limited as long as the α carbon atom is an asymmetric carbon atom. In one aspect of the present invention, an α-amino acid having the amino group bound to the α carbon atom is preferred. In one aspect of the present invention, in terms of manufacturing an amino acid derivative for synthesizing a peptide or a protein, the amino acid is preferably a natural or non-natural protein-constituting amino acid. In one aspect of the present invention, in terms of manufacturing an amino acid having almost substantially the same amino acid sequence as a protein that exists in vivo, the amino acid is preferably a natural amino acid.

An amino acid derivative as used herein comprises those where the side chain substituent of the amino acid is substituted by further another substituent, and those that are derivatized by having a protecting group or other substituents bound to the functional groups such as amino group or carboxyl group. In other words, an amino acid derivative as used herein is employed to generically refer to amino acids including those that are derivatized such as these examples, but does not intend to exclude a non-derivatized amino acid.

When the amino acid is an α amino acid having the amino group bound to the α carbon atom of the amino acid, if the other two substituents bound to the α carbon atom are not the same substituent (such as a hydrogen atom), the α carbon atom is an asymmetric atom, and enantiomers referred to as D- and L-forms exist. As used herein, a D-form amino acid is referred to as a "D-amino acid" or a "D-form amino acid" and the like, and a L-form amino acid is referred to as a "L-amino acid" or a "L-form amino acid" and the like.

In case of an amino acid derivative in which the β carbon atom is also an asymmetric carbon atom, optical isomers having the β carbon atom as the chiral center will also exist. When referring to a D- or L-form for the α carbon atom herein, the abundance ratio of the optical isomers for the β carbon atom may be arbitrary. In other words, optical isomers for the β carbon atom may be in an optically resolved state, or optical isomers for the β carbon atom may be comprised at an arbitrary ratio. In other words, when referring to an optically active amino acid derivative herein, it may be in an optically active form in which optical isomers for at least the α carbon atom are optically resolved.

Moreover, as used herein, when there is an equal mixture of D- and L-forms for the α carbon atom, the amino acid derivative is also referred to as a racemate or a racemic amino acid derivative. As is ordinarily broadly interpreted, a racemate may be an equal mixture of D- and L-forms in the practical sense, or may be those that exist in forms referred to as a racemic mixture, a racemic compound, and a racemic solid solution.

In one aspect of the present invention, the present invention relates to a method of manufacturing a D- or L-amino acid derivative possessing a protected or non-protected thiol group at the β-position. Here, possessing substituent R at the β-position is the same meaning as having substituent R bound to the β carbon atom.

"A protected or non-protected" substituent R as used herein refers to substituent R protected by a protecting group or an unprotected substituent R. For example, "a protected or non-protected thiol group" refers to a thiol group protected by a protecting group or an unprotected thiol group. The protecting group for the thiol group is not limited in any way as long as it can be employed as a protecting group for the thiol group. Examples of a protecting group for the thiol group include e.g. a PMB (paramethoxybenzyl) group, an Acm (acetamidomethyl) group, a benzyl group, a Trt (trityl) group, a disulfide group, and a t-butyl group.

"A non-natural D- or L-amino acid derivative possessing a protected or non-protected thiol group at the β-position" herein refers that an amino acid in the state possessing a protected or non-protected thiol group at the β-position is a non-natural amino acid. In other words, cysteine which is known as a natural amino acid is an amino acid possessing a non-protected thiol group at the β-position, and is a natural amino acid in the state possessing a thiol group at the β-position. "A non-natural D- or L-amino acid derivative possessing a protected or non-protected thiol group at the β-position" means that it does not comprise such a natural cysteine. In other words, "a non-natural D- or L-amino acid derivative possessing a protected or non-protected thiol group at the β-position" does not intend to exclude "an amino acid having a protected or non-protected thiol group introduced at the β-position of a natural amino acid" or a derivative thereof. An amino acid derivative possessing a protected or non-protected thiol group at the β-position is also referred to herein as a "β-thioamino acid derivative."

In one aspect of the present invention, in terms of obtaining an amino acid that can be employed in the NCL linking site for synthesizing a protein configured by natural amino acids, a β-thioamino acid derivative as the compound of interest in the present invention is preferably an amino acid in which a protected or non-protected thiol group is bound instead of one of the hydrogen atoms bound to the β carbon atom of a natural amino acid, or a derivative thereof.

One example of such a β-thioamino acid derivatives can be shown as compounds described in the following chemical formulae corresponding to each natural amino acid.

[Chemical Formula 3]

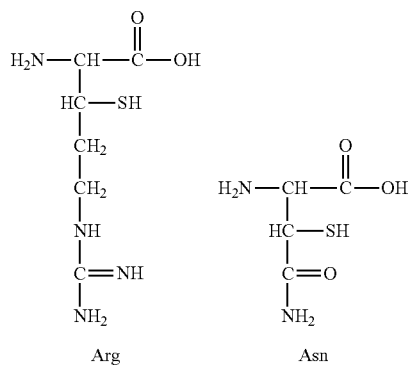

Arg     Asn

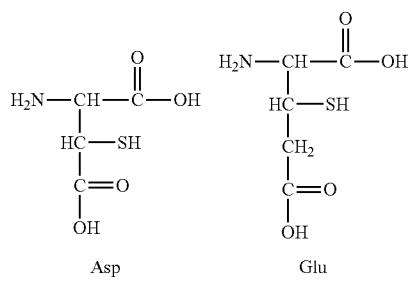

Asp     Glu

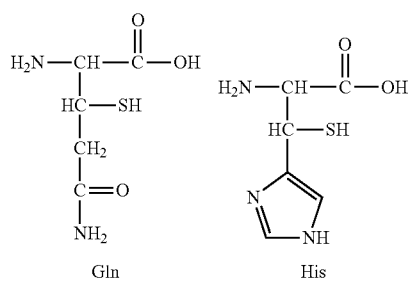

Gln     His

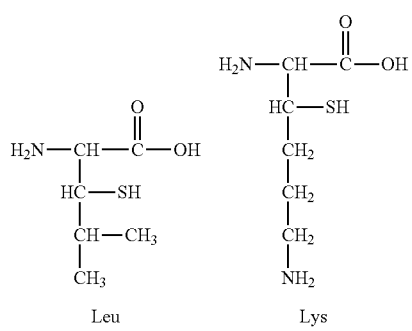

Leu     Lys

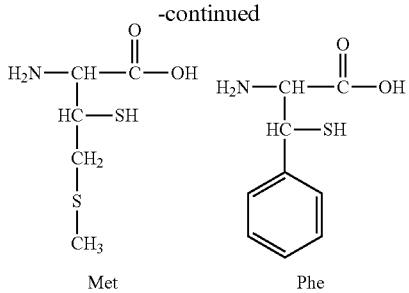

Met     Phe

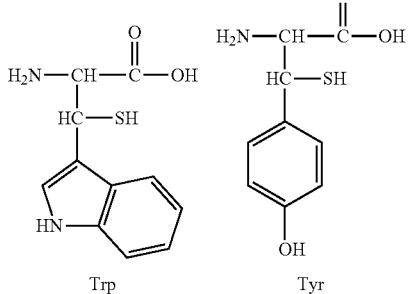

Trp     Tyr

In these chemical formulae, D- and L-forms are described without discriminating stereoisomerism, but if D- and L-forms were described as stereoisomers, the compounds described in these chemical formulae can be represented by the example following two chemical formulae, e.g. when the natural amino acid is phenylalanine. In the following two chemical formulae, the L-form is on the left and the D-form is on the right. Other compounds described in the above chemical formulae can similarly be described as D- and L-forms.

[Chemical Formula 4]

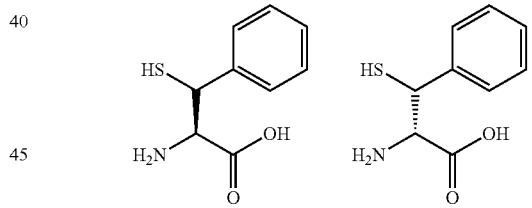

Moreover, in the above chemical formulae as one example of β-thioamino acid derivatives corresponding to each natural amino acid as described above, a most simplified example in which the amino group, the carboxy group, and other side chain substituents are not protected nor substituted was described, but compounds having these amino groups, carboxyl groups, and other side chain substituents substituted by a protecting group or other substituents are included in "a non-natural amino acid derivative possessing a protected or non-protected thiol group at the β-position."

In one aspect of the present invention, a β-thioamino acid derivative as the compound of interest in the present invention can also be referred to as an amino acid derivative possessing a protected or non-protected thiol group at the β-position, and also has substituent $R^1$ at the β-position. Here, $R^1$ refers to the substituent moiety bound to the β carbon atom among side chain substituents that configure amino acids that is not a hydrogen atom. In the phenylalanine example, since phenylalanine is an amino acid having two hydrogen atoms and a phenyl group bound at the β-position, $R^1$ is a phenyl group. Substituent $R^1$ can be similarly comprehended for each natural amino acid. For example, when the natural amino acid is Asn or Gln, substituent $R^1$ is respectively —CO—$NH_2$ or —$CH_2$—CO—$NH_2$. When the natural amino acid is Trp, Tyr, or His, substituent $R^1$ is respectively an indol-3-yl group, a -para-hydroxyphenyl group, or a 1H-imidazo-4-yl group. When the natural amino acid is Asp or Glu, substituent $R^1$ is respectively —COOH or —$CH_2$—COOH. When the natural amino acid is Arg or Lys, substituent $R^1$ is respectively —$(CH_2)_2$—NH—$C(NH_2)_2$ or —$(CH_2)_3$—$NH_2$. When the natural amino acid is Met or Leu, substituent $R^1$ is respectively —$CH_2$—$SCH_3$ or —$CH(CH_3)_2$. The carboxyl group and amino groups etc. comprised in these substituents $R^1$ may be a free acid or base, or may be a salt. Moreover, those skilled in the art will be able to similarly recognize respective substituent $R^1$ even for non-natural amino acids as the substituent moiety bound to the β carbon atom that is not a hydrogen atom from its amino acid structural formula. Moreover, when substituent $R^1$ comprises a group with high reactivity such as a functional group, it is preferred that these groups are protected by a protecting group, substituted by another substituent, or converted into another substituent.

An amino acid derivative possessing a protected or non-protected thiol group at the β-position is sometimes referred to herein as a β-thioamino acid derivative. Moreover, an amino acid possessing the side chain substituent of a natural amino acid, wherein the amino acid derivative has a protected or non-protected thiol group introduced instead of a hydrogen atom bound to its β carbon atom, is sometimes referred to as a β-thioamino acid derivative of a natural amino acid. For example, in the case of phenylalanine, the amino acid derivative represented by the above structural formula can be referred to as the β-thioamino acid derivative of phenylalanine. Moreover, an amino acid derivative as an equal mixture of D- and L-forms is sometimes referred to as a D,L-β-thioamino acid derivative.

As one aspect of the present invention, the manufacturing method of the present invention relates to a method of manufacturing a non-natural D- or L-amino acid derivative possessing a protected or non-protected thiol group at the β-position. In this manufacturing method, after manufacturing an amino acid derivative possessing a thiol group at the β-position as an intermediate composition comprising D- and L-forms, a hydrolase selective for D- or L-amino acids is reacted to separate D- or L-amino acid derivatives. Because the above intermediate composition is manufactured as an amino acid derivative that possesses a moiety to be the substrate for a hydrolase selective for D- or L-forms, it can also be referred to as a composition possessing the substrate moiety of a hydrolase selective for D- or L-amino acids that comprises D- and L-forms of the β-thioamino acid derivative.

The β-thioamino acid derivative possessing the substrate moiety of a hydrolase selective for D- or L-amino acids may be manufactured by introducing a thiol group at the β-position of an amino acid derivative possessing the substrate moiety of a hydrolase selective for D- or L-amino acids. Alternatively, it may be manufactured by converting a substituent of the β-thioamino acid derivative in order to possess a substrate moiety of a hydrolase selective for D- or L-amino acids. Moreover, the β-thioamino acid derivative may be manufactured by introducing a thiol group at the β-position of an amino acid derivative, or it may be manufactured by e.g. a method of condensing an amino acid derivative and a thiol group-containing compound. A method of converting a substituent in order to allow it to be a substrate moiety of a hydrolase selective for D- or L-amino acids can be carried out by converting the amino group or carboxyl group bound to the α carbon atom of an amino acid into a substrate for a hydrolase selective for D- or L-forms. In this reaction, the amino group or carboxyl group before the conversion reaction may be an unprotected amino group or carboxyl group, or may be an amino group or carboxyl group protected by other protecting groups.

The β-thioamino acid derivative possessing the substrate moiety of a hydrolase selective for D- or L-amino acids as the above intermediate can be manufactured by a manufacturing method that does not control stereoisomerism for the α carbon atom. By not controlling stereoisomerism for the α carbon atom, the above β-thioamino acid derivative possessing the substrate moiety of a hydrolase selective for D- or L-amino acids can be obtained as a composition comprising D- and L-forms.

By reacting the above β-thioamino acid derivative possessing the substrate moiety of a hydrolase selective for D- or L-amino acids comprising D- and L-forms with a hydrolase selective for D- or L-amino acids, the D- or L-amino acid derivative is selectively hydrolyzed. In a state that the amino group or carboxyl group produced by hydrolysis is still unprotected or is protected by a protecting group, the hydrolyzed D- or L-amino acid derivative and unhydrolyzed other amino acid derivative can be separated by their difference in hydrophobicity etc.

The present invention, as one aspect thereof, can be represented by a manufacturing method comprising the following steps (I) and (II):

(I) manufacturing an amino acid derivative possessing a protected or non-protected thiol group at the β-position comprising D- and L-forms, and (II) reacting the amino acid derivative obtained in (I) with a hydrolase selective for either one of D- or L-amino acids, and subsequently separating the hydrolyzed D- or L-amino acid derivative.

"Comprises D- and L-forms" herein refers to comprising D- and L-forms as optical isomers for the α carbon atom, and unless particularly described, the ratio of the amount thereof is not to be specified. In one preferred aspect of the present invention, this means substantially comprising both D- and L-forms. Moreover, in one aspect of the present invention, this can be an equal mixture of D- and L-forms.

In one aspect of the present invention, step (I) can be expressed as a step of carrying out the following reactions (A) and (B) on the amino acid derivative to manufacture an amino acid derivative possessing a protected or non-protected thiol group at the β-position comprising D- and L-forms:

(A) a reaction of introducing a protected or non-protected thiol group at the β carbon atom of the amino acid derivative, and (B) a reaction of converting the amino group or carboxyl group bound to the α carbon atom of an amino acid derivative into a substituent to be the substrate for a hydrolase selective for D- or L-amino acids.

Here, the order of the above reactions (A) and (B) may be carried out in the order of (A), (B) or in the order of (B), (A). Moreover, in addition to (A) and (B), other reactions such as protection and deprotection on the functional group or substituent of the amino acid derivative can also be appropriately carried out. Moreover, reactions (A) and (B) etc. are described herein but these can also be referred to as step (A) and (B) etc.

Step (I), "a step of carrying out the following reactions on an amino acid derivative to manufacture an amino acid derivative possessing a protected or non-protected thiol group at the β-position comprising D- and L-forms" may realize a state of comprising D- and L-forms after carrying out the reaction included in step (I), the amino acid to be the raw material may be an amino acid composed substantially of one of D- or L-form or a derivative thereof, or may be an amino acid in which the α carbon atom is not an asymmetric carbon atom such as glycine or a derivative thereof. Moreover, in one aspect of the present invention, in terms of efficiently recrystallizing the amino acid derivative obtained in step (I), it is preferred to comprise D- and L-forms at equal amounts. Comprising D- and L-forms at equal amounts may be at an equal amount in the practical sense. In other words, in one aspect of the present invention, it is preferred that the intermediate composition of the amino acid derivative obtained in step (I) is racemic.

The reaction of introducing a protected or non-protected thiol group at the β carbon atom of the amino acid derivative is not particularly limited as long as it is a reaction that introduces a protected or non-protected thiol group at the β carbon atom of the amino acid derivative. Introduction may also be carried out after introducing a leaving group at the β carbon atom of the amino acid derivative as an exchange reaction with the leaving group.

For example, this reaction can be carried out by reacting the amino acid derivative with a thiol compound. In terms of introducing a protected thiol group, it is preferred to employ a thiol compound having a protecting group and a hydrogen atom bound to the sulfur atom. Thiol compounds can include benzyl mercaptans or tritylthiols that may possess any number of substituents such as a halogen atom such as fluorine, chlorine, bromine, and iodine, an lower alkyl group having 1-4 carbons such as a methyl group and an ethyl group, an alkoxy group having 1-4 carbons such as a methoxy group and an ethoxy group, and a nitro group at any position on the phenyl ring, alkanethiols such as methanethiol, ethanthiol, and t-butanethiol, acyl thiols that can be easily converted into an acetamidomethyl group, a trityl group, and a disulfide group, and the like.

The amount of the thiol compound used may be 1-100 equivalents, preferably 2-20 equivalents, and further preferably 3-10 equivalents to 1 equivalent of the amino acid derivative to be the raw material. Examples of the solvent used can include THF, DCM, DMSO, DMF, and the like, and among these DMF is preferred. The reaction can be carried out in a reaction condition of e.g. at 1-100° C., preferably 10-80° C., and further preferably 15-35° C. for 30 minutes-24 hours, preferably, 1-12 hours, and further preferably 2-6 hours reaction.

The raw material compound of this reaction may be an amino acid or an amino acid derivative that can have a thiol group introduced at the β-position. In other words, the raw material compound may be an amino acid, or may be an amino acid derivative having the amino group, carboxyl group, side chain substituent, and the like of the amino acid protected or substituted by a substituent. In one aspect of the present invention, in terms of efficiently carrying out the reaction, it is preferably an amino acid derivative possessing a leaving group at the β-position, and more preferably an amino acid derivative possessing a halogen atom at the β-position. Moreover, in one aspect of the present invention, in terms of preventing side reactions to increase the yield, it is preferably an amino acid derivative having the amino group and carboxyl group of the amino acid protected.

The reaction of converting the amino group or carboxyl group bound to the α carbon atom of an amino acid derivative into a substituent to be the substrate for a hydrolase selective for D- or L-amino acids is not particularly limited as long as it is a reaction that yields an amino acid derivative having a substituent to be the substrate for a hydrolase selective for D- or L-amino acids bound to the α carbon atom after the reaction. "The amino group or carboxyl group bound to the α carbon atom of an amino acid derivative" in the starting material of the reaction may be a protected or non-protected amino group or carboxyl group. In other words, it may be an unprotected free amino group or carboxyl group, or it may be an amino group or carboxyl group protected by a protecting group. In one aspect of the present invention, when carrying out this reaction after introducing a thiol group at the β-position of the amino acid derivative, if an amino acid derivative having a thiol group introduced at the β-position is used as the raw material and the amino group and carboxyl group are protected for thiolation, the reaction can be carried out using an amino acid derivative having these protected as the raw material.

A group that can be generally employed as the protecting group of the amino group can be employed as the protecting group of the amino group, and e.g. a lipophilic protecting group described below etc. can be employed. For example, in one aspect of the present invention, examples can include a protecting group such as a 9-fluorenylmethoxycarbonyl (Fmoc) group or a t-butyloxycarbonyl (Boc) group, a carbonate-containing group such as an allyloxy carbonate (Alloc) group, an acyl group such as an acetyl (Ac) group, an aryl group, a benzyl group, and the like. In order to introduce a protecting group, e.g. when introducing a Boc group, this can be carried out by e.g. a method of adding a THF solution of $Boc_2O$ to the reaction system. The introduction of the protecting group of the amino group can be carried out with the above method as well as well-known methods according to the protecting group. Moreover, the deprotection of the protecting group of the amino group can be carried out by treatment with an acid or a base. For example, when the protecting group is a Boc group, an acid such as trifluoroacetic acid (TFA) can be used. In doing so, this is preferably carried out in the presence of a solvent, examples of which can include DCM, THF, acetonitrile, and the like. The deprotection of the protecting group of the amino group can be carried out with the above method as well as ordinary methods.

A group that can be generally employed as the protecting group of the carboxyl group can be employed as the protecting group of the carboxyl group, for example a lipophilic protecting group described below etc. can be employed. For example, in one aspect of the present invention, examples include protection as an ester by an alkyl group such as a methyl group, an ethyl group, and a tert-butyl group, or an arylalkyl group such as a benzyl group. When the protecting group of the carboxyl group is a methyl group, methyl esterification can be carried out e.g. by a method of adding thionyl chloride and methanol. The introduction of the protecting group of the carboxyl group can be carried out with the above method as well as well-known methods depending on the protecting group. Moreover, the deprotection of the protecting group of the carboxyl group can be carried out by treatment with an acid or a base. For example, when the protecting group is a methyl group, a base such as sodium hydroxide can be used. In doing so, this is preferably carried out in the presence of a solvent, examples of which can include THF, dioxane, acetonitrile, and the like. The deprotection of the protecting group of the carboxyl group can be carried out with the above method as well as ordinary methods.

The "hydrolase selective for D- or L-amino acids" is not particularly limited as long as it is an enzyme that hydrolyzes selectively for D-form amino acids or an enzyme that hydrolyzes selectively for L-form amino acids. Examples of a hydrolase can include an amidase, a protease, an esterase, a lipase, and the like. The origin of these enzymes is not particularly limited, and may be microorganism-derived such as bacteria, or may be mammal-derived. Those commercially available are employed as these hydrolases selective for D- or L-amino acids, or they can also be prepared by well-known methods. Examples of those commercially available can include an acylase "Amano" (aminoacylase selective for L-acyl form) (from Amano Enzyme Inc.), a D-aminoacylase "Amano" (aminoacylase selective for D-acyl form) (from Amano Enzyme Inc.), and the like.

In one aspect of the present invention, in terms of simplifying separation after enzyme reaction and efficiently obtaining D- or L-forms, it is preferred to employ a D- or L-aminoacylase as the "hydrolase selective for D- or L-amino acids." In the manufacturing method of the present invention, the method of separating the hydrolyzed D- and L-forms by a hydrolase is not particularly limited as long as separation is possible. In one aspect of the present invention, the hydrolyzed D- or L-amino acid derivative and the unhydrolyzed other amino acid derivative can be efficiently separated by introducing a lipophilic protecting group into the hydrolyzed amino group or carboxyl group. In such a separation, the extent of the difference in hydrophobicity between the acylamino group and the amino group protected by one or two lipophilic amino protecting groups is to be relatively large, and it is preferred in terms of enabling efficient separation that an aminoacylase is selected as the hydrolase. A separation step employing such a protecting group will be described below.

"Selective for D- or L-amino acids" may be those having selectivity for D- or L-form, and is not limited to those that are 100% or close thereto. In the present invention, in terms of manufacturing an optically active amino acid having high purity of D- or L-form, those having high selectivity for D- or L-form are preferred, and in effect those that react to only one of D- or L-form are more preferred.

As the "reaction of converting into a substituent to be the substrate for a hydrolase selective for D- or L-amino acids," the protected or non-protected amino group or carboxyl group bound to the α carbon atom can be converted in order to allow it to be the substrate of the selected enzyme depending on the selection of the above enzyme. In other words, the protected or non-protected amino group or carboxyl group can be converted with an ordinary method according to the type or structure of the substituent of interest. For example, when employing aminoacylase as the enzyme, by acylating the protected or non-protected amino group, it can be converted into an aminoacyl group as the substrate of the enzyme.

For example, a method of acylating the amino group can be carried out by e.g. a method of reacting an amino acid derivative possessing a protected or non-protected amino group with a carboxylic acid halide or a carboxylic acid anhydride. Moreover, for example, the acetylation of the amino group can be carried out by e.g. a method of adding acetic anhydride ($Ac_2O$) to a reaction system comprising an amino acid derivative possessing a protected or non-protected amino group and allowing to react. The solvent is not particularly limited as long as it is a solvent that allows aminoacylation to proceed, and for example water, methanol, ethanol, THF, DCM etc., or a mixed solvent thereof and the like can be employed. The reaction temperature is not particularly limited as long as it is a temperature that allows aminoacylation to proceed. The temperature can be e.g. 0-40° C. and the like, and can be carried out at an ordinary room temperature. The reaction time may be a time sufficient to allow aminoacylation to proceed, and for example can be 1 minute-10 hours, preferably 5 minutes-1 hour and the like.

The reaction can be carried out by well-known methods when employing aminoacylase as the enzyme, as well as when employing amidase, protease, esterase, lipase, and the like. When employing an amidase, the reaction can be carried out by a reaction of amidating a protected or non-protected amino group, or by a reaction of amidating a protected or non-protected carboxyl group. Moreover, when employing an esterase, the reaction can be carried out by a reaction of esterifying a protected or non-protected carboxyl group. Those skilled in the art will be able to refer to the description herein and similarly in accord thereto carry out the reaction in case of employing other hydrolases.

When protecting the amino group or carboxyl group by a protecting group, it is also possible that the amino group or carboxyl group protected by a protecting group will per se become the substrate for a hydrolase selective for D- or L-amino acids. In such a case, the step of protecting the amino group or carboxyl group by a protecting group can be referred to as a reaction of converting into a substituent to be the substrate for a hydrolase selective for D- or L-amino acids. In one aspect of the present invention, in terms of reducing the number of steps in the manufacturing method of the present invention, it is also preferred that the reaction of converting into a substituent to be the substrate for a hydrolase selective for D- or L-amino acids is first carried out, the amino group and carboxyl group are protected, and then a thiol group is introduced at the β-position.

In one aspect of the present invention, when employing a substituent with relatively high reactivity as the substituent to be the substrate for a hydrolase selective for D- or L-amino acids, it is preferred that the reaction of converting into a substituent to be the substrate for a hydrolase selective for D- or L-amino acids is carried out immediately before the hydrolysis reaction by the enzyme. Moreover, in such a case, when carrying out the reaction of introducing a thiol group at the β-position, it is preferred that the amino group and carboxyl group are separately protected by a protecting group.

In this case, the above step (I) can also be expressed as follows. In other words, step (I) can also be expressed as a step of preparing an amino acid derivative having the amino group and carboxyl group comprised in the amino acid to be the raw material protected by a protecting group, and carrying out the following reactions on the amino acid derivative to manufacture an amino acid derivative possessing a protected or non-protected thiol group at the β-position comprising D- and L-forms:

(A) a reaction of introducing a protected or non-protected thiol group at the β carbon atom of said amino acid derivative, and (B) a reaction of converting a protected amino group or a protected carboxyl group bound to the α carbon atom of said amino acid derivative into a substituent to be the substrate for a hydrolase selective for D- or L-amino acids.

Moreover, when other functional groups are present in the amino acid to be the raw material, it can also be expressed as a step of preparing an amino acid derivative having the amino group, the carboxyl group, and other functional groups comprised in the amino acid to be the raw material protected by a protecting group.

In one aspect of the present invention, the hydrolase selective for D- or L-amino acids can be selected according to various elements to consider such as degree of stereoselectivity, ease of availability, and ease of conversion of the amino group or carboxyl group of the amino acid derivative into the substrate. Separating the step of protecting the amino group or carboxyl group of the amino acid derivative and the step of converting into the substrate of the enzyme is preferred in that it allows selecting of a hydrolase having such a substituent as the substrate even when the reactivity of the substituent to be the substrate of the enzyme is high.

In one aspect of the present invention, an amino acid derivative having a thiol group introduced at the β-position and having the amino group or carboxyl group converted into the substrate of the hydrolase by the above reaction can be separated and purified by a method such as recrystallization before being employed for the next step. The method of purification can be carried out by ordinary methods such as recrystallization, silica gel column, and extraction by an organic solvent.

The present inventors found that in one aspect of the manufacturing method of the present invention, when an amino acid derivative having a thiol group introduced at the β-position and having the amino group or carboxyl group converted into the substrate of the hydrolase is an equal mixture of D- and L-forms, this intermediate composition in particular can be efficiently recrystallized. An equal mixture of D- and L-forms can also be referred to as a racemate for the α carbon atom, or simply a racemate.

When recrystallizing such an intermediate composition, crude product may be obtained beforehand with e.g. extraction by an organic solvent. Extraction by an organic solvent can be carried out by ordinary methods. When carrying out recrystallization, an organic solvent such ethyl acetate, methanol, ethanol, and ether, or a mixed solvent thereof and the like can be employed as the solvent. Preferably, methanol, ether, and the like can be employed.

In the manufacturing method of the present invention, a step of reacting the amino acid derivative obtained in the above step (I) with a hydrolase selective for either one of D- or L-amino acids, and subsequently separating the hydrolyzed D- or L-amino acid derivative is carried out as step (II).

By reacting an amino acid derivative comprising D- and L-forms obtained by the above step (I) with a hydrolase selective for either one of D- or L-amino acids, the amino acid derivative comprising either one of D- and L-forms will be selectively hydrolyzed by the above hydrolase due to the stereoselectivity of the enzyme. For example, if a hydrolase selective for D-amino acids is reacted, the D-form amino acid derivative is selectively hydrolyzed. Moreover, if a hydrolase selective for L-amino acids is reacted, the L-amino acid is selectively hydrolyzed.

The hydrolase selective for D- or L-amino acids is as described above. The hydrolysis reaction can be carried out similarly to a general enzyme reaction. The hydrolase selective for D- or L-amino acids can be employed as an enzyme solution prepared by dissolving it in various buffers ordinarily employed for enzyme reactions. The buffer is not particularly limited as long as it is a buffer that can allow enzyme reaction to proceed, and for example phosphate buffer, tris hydrochloride salt, and the like can be employed. The reaction can be carried out at a pH of 6.0-10.0, and the pH can be preferably 7.0-9.0, more preferably 8.0. Moreover, the amount of the enzyme employed in the hydrolysis reaction is not particularly limited as long as it is an amount that allows the hydrolysis reaction to efficiently proceed, and e.g. a catalytic amount or an excess amount to the substrate can be employed. In terms of allowing the hydrolysis reaction to efficiently proceed, for example the amount can be 0.1-10000 units, preferably 1-1000 units to 100 mg of the substrate. Moreover, the reaction can be carried out at a reaction temperature of 10° C.-60° C., preferably 20° C.-55° C., and more preferably 30° C.-50° C. The reaction time can be 1 hour-30 days, preferably 12 hours-20 days, and more preferably 2-14 days.

In the manufacturing method of the present invention, step (II) comprises a step of separating the hydrolyzed D- or L-amino acid derivative after the hydrolysis reaction by the above enzyme. In step (II), when referred to as carrying out the hydrolysis reaction and "subsequently" carrying out a step of separation, the separation step may be carried out after the hydrolysis reaction, and this hydrolysis reaction and the separation reaction are not limited to being carried out in a directly consecutive manner. For example, the free amino group or carboxyl group produced by hydrolysis may be subjected to a separation step still in an unprotected state, or may be subjected to a separation step after a step of protecting the free amino group or carboxyl group by a protecting group and the like. In one aspect of the present invention, it is preferred to be protected by an appropriate protecting group in order to efficiently carry out the subsequent separation step.

In step (II), the step of separating the hydrolyzed D- or L-amino acid derivative is not limited in any way as long as it is a method that separates the hydrolyzed one enantiomer and the unhydrolyzed other enantiomer from each other. For example, a method of retrieving only one from the reaction system, a method of removing one from the reaction system, a method of localizing one or the other respectively in an organic phase and an aqueous phase, and a method of retrieving both from the reaction system and fractioning one or both respectively with a separation and purification means such as chromatography and the like can be employed.

For example, the method of manufacturing a non-natural D-amino acid derivative possessing a thiol group at the β-position can be carried out by reacting an intermediate composition comprising D- and L-forms possessing a thiol group at the β-position with a hydrolase selective for D-amino acids, and subsequently separating the hydrolyzed D-amino acid derivative.

On the other hand, the method of manufacturing a non-natural L-amino acid derivative possessing a thiol group at the β-position can be carried out by reacting an intermediate composition comprising D- and L-forms possessing a thiol group at the β-position with a hydrolase selective for L-amino acids, and subsequently separating the hydrolyzed L-amino acid derivative.

Here, for example, separation of the hydrolyzed D-form is not limited to the method of retrieving the D-form from the reaction system, and it may be e.g. a method of separating the D-form by removing the unhydrolyzed unreacted material from the reaction system. These methods can be carried out for example by well-known methods such as extraction, crystallization, silica gel column chromatography, and high performance liquid chromatography (HPLC).

In one preferred aspect of the present invention, since the other enantiomer can also be utilized after separating one enantiomer, a method of fractioning the other after first fractioning one, or a method of purifying and fractioning each of both by employing silica gel column chromatography etc. is preferred. Moreover, D- and L-forms may be fractioned after obtaining a crude product by extraction, crystallization, and the like.

In one aspect of the present invention, the step of separating the hydrolyzed D- or L-amino acid derivative comprises a step of introducing a lipophilic protecting group into the hydrolyzed D- or L-amino acid derivative, and can be a step of utilizing the difference in hydrophobicity produced by the presence or absence and/or the number of the lipophilic protecting group to separate the D- or L-amino acid derivative having the lipophilic protecting group introduced.

The lipophilic protecting group employed here is not particularly limited as long as it is employed as a protecting group of the amino group or carboxyl group and is lipophilic. Examples of a lipophilic protecting group of the amino group include a lipophilic protecting group selected from carbamates, acyls, imides, alkyls, sulfonamides. Examples of a carbamate protecting group include a Boc group, a Fmoc group, a 2,2,2-trichloroethoxycarbonyl (Troc) group, a benzyloxycarbonyl (Cbz) group, and an Alloc group. An Example of an acyl protecting group includes an acetyl (Ac) group, an example of an imide protecting group includes a phthaloyl (Pht) group, examples of an alkyl protecting group include a trityl (Trt) group, a benzyl group, and an aryl group, and examples of a sulfonamide protecting group include a p-toluene sulfonyl group (Ts or Tos) group and 2-nitrobenzene sulfonyl (Ns) group. Moreover, lipophilic protecting groups of the carboxyl group include a lipophilic protecting group selected from esters, amides, and the like. Examples of an ester protecting group include an alkyl group ester such as a methyl group, an ethyl group, and a tert-butyl group, and an arylalkyl group ester such as a benzyl group.

In one aspect of the present invention, in terms of utilizing the difference in hydrophobicity produced by the lipophilic protecting group to separate the D- or L-amino acid derivative having the lipophilic protecting group introduced, it is preferred that the substituent as the enzyme substrate moiety and the lipophilic protecting group are selected so that the difference in hydrophobicity with the amino group or carboxyl group converted into the enzyme substrate moiety will be large. As one aspect of the present invention, when employing aminoacylase as the hydrolase, it is preferred to protect the amino group after hydrolysis by a carbamate lipophilic protecting group, particularly preferably a Boc group, a Fmoc group, a Cbz group, an Alloc group, and the like.

In one aspect of the present invention, when employing a lipophilic protecting group, the difference in hydrophobicity produced by the presence or absence and/or the number of the lipophilic protecting group can be utilized to separate the D- or L-amino acid derivative having the lipophilic protecting group introduced. For example, when employing a Boc group as the lipophilic protecting group, the amino group will become a —NH Boc group if one protecting group is introduced for one amino group. Moreover, if two protecting groups are introduced for one amino group, the amino group will become a —N(Boc)$_2$ group which can also be referred to as a —N,N-diBoc group. Separation may be carried out in any of these states as the separation step in the manufacturing method of the present invention. Moreover, when the group produced by hydrolysis is a carboxyl group, separation can be similarly carried out with a method of separating directly as a free carboxyl group, as well as by introducing one protecting group for one oxygen atom configuring the carboxyl group. Utilizing the difference in hydrophobicity can also be referred to as utilizing the difference in hydrophilicity. Moreover, in one aspect of the present invention, it can also be referred to as utilizing the difference in solubility to a solvent such as an extraction solvent by introducing a lipophilic protecting group, or utilizing the difference in affinity to a solid phase such as a column when employing column chromatography etc. Further, depending on the separation method, separation can be also be carried out by utilizing the bulkiness of the protecting group. Moreover, separation can also be carried out by utilizing the difference in the electric charge of the compound produced by the presence or absence of mainly the protecting group.

In one aspect of the present invention, examples of a method of utilizing the difference in hydrophobicity produced by the presence or absence and/or the number of the lipophilic protecting group to separate the D- or L-amino acid derivative having the lipophilic protecting group introduced that can be employed are a method by extraction, a method by silica gel column chromatography, and the like. In one aspect of the present invention, in terms of efficiently separating and purifying the amino acid of the present invention, it is preferred to employ silica gel column chromatography. When carrying out separation and purification by silica gel column chromatography, a commercially available silica gel filled into a glass tube can be prepared and employed as the column. The silica gel employed for the column is not particularly limited as long as it enables separation of the amino acid derivative of the present invention by e.g. the presence or absence of the lipophilic protecting group, and for example Silica gel 60 (40-63 μm) (from Merck KGaA) and the like can be employed. The glass tube employed for the column is not particularly limited as long as it enables filling of silica gel and separation of the amino acid derivative, and for example a chromatograph tube (no filter, with stopcock) (from AS ONE Corporation) and the like may be employed. The developing solvent (elution solvent) may be a solvent ordinarily employed in silica gel column chromatography, and for example, hexane, ethyl acetate, dichloromethane (DCM), methanol, acetonitrile etc., or a mixed solvent thereof and the like can be employed. In one aspect of the present invention, it is preferred to employ a developing solvent of ethyl acetate:hexane=1:1-10, 1% formic acid-containing ethyl acetate, and the like. Those skilled in the art will be able to select and employ a developing solvent according to the structure etc. of the amino acid derivative of interest based on the description herein.

In one aspect of the present invention, both D- and L-forms of an amino acid derivative possessing a thiol group at the β-position may be obtained as optically active amino acid derivatives. In particular, in terms of obtaining D- and L-form amino acid derivatives employed for synthesis of racemic proteins and the like, it is preferred to obtain both D- and L-forms as optically active amino acid derivatives. In this case, in terms of obtaining each of substantially the same amount of D- and L-forms, it is preferred to employ a racemic amino acid or glycine as the raw material compound.

In this case, for example, the subject compound can be obtained by carrying out a step of reacting an intermediate composition comprising D- and L-forms with e.g. a hydrolase selective for D-amino acids, and subsequently a step of separating the hydrolyzed D-amino acid derivative simultaneously with, or before or after carrying out a step of obtaining the unhydrolyzed L-amino acid derivative.

On the other hand, the subject compound can be obtained by carrying out a step of reacting an intermediate composition comprising D- and L-forms with e.g. a hydrolase selective for L-amino acids, and subsequently separating the hydrolyzed L-amino acid derivative simultaneously with, or before or after carrying out a step of obtaining the unhydrolyzed D-amino acid derivative.

Here, a step of separating the hydrolyzed one amino acid derivative and simultaneously obtaining the other amino acid derivative can be carried out by obtaining each fraction in silica gel column chromatography. Moreover, obtaining the other amino acid derivative before or after a step of separating the hydrolyzed one amino acid derivative can be carried out by separating one amino acid derivative with methods such as extraction and recrystallization, and then separating the other amino acid derivative.

In one aspect of the present invention, when obtaining both D- and L-forms of an amino acid derivative possessing a thiol group at the β-position as optically active amino acid derivatives, the unhydrolyzed amino acid derivative may also be hydrolyzed according to the objective by a hydrolase selective for D- or L-amino acids. This hydrolysis may be carried out by reacting an amino acid derivative composition comprising D- or L-forms with a hydrolase selective for D- or L-amino acids. Moreover, the hydrolysis reaction may be carried out by a hydrolase without stereoselectivity after separating D- and L-form amino acid derivatives, or as an ordinary chemical reaction without an enzyme etc.

In one aspect of the present invention, when aminoacylase is employed as the enzyme selective for D- or L-forms, the intermediate obtained by step (I) can be represented by the following structural formula.

[Chemical Formula 5]

The above chemical formula is described without discriminating the presence of stereoisomers for α and β asymmetric carbon atoms. In one aspect of the present invention, intermediates can be represented as such in that intermediates can be manufactured without discriminating stereoisomers for these asymmetric carbon atoms. In fact, since optical isomerism for the α carbon atom and optical isomerism for the β carbon atom exist, four types of diastereomers produced by combination of these may be comprised at an arbitrary proportion.

In one aspect of the present invention, a β-thioamino acid derivative intermediate composition possessing the substrate moiety for an aminoacylase comprising D- and L-forms can also be represented as a composition comprising D- and L-forms represented by the following two chemical formulae. In the following chemical formulae, the L-form is on the left and the D-form is on the right.

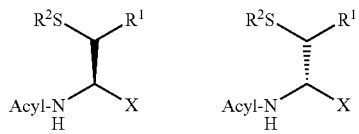

[Chemical Formula 6]

Here, $R^2$—S indicates a thiol group introduced at the β carbon atom. The thiol group may be an unprotected thiol group or a thiol group protected by a protecting group. The protecting group for the thiol group is as described above. The presence or absence of a protecting group for the thiol group and the protecting group to be employed can be appropriately determined in the manufacturing method of the present invention according to the compound of interest. For example, in terms of preventing the thiol group from reacting during the manufacturing method of the present invention, it is preferred that the thiol group is protected. It is also preferred that the thiol group is protected when obtaining a D- or L-selective amino acid derivative possessing a protected thiol group as the compound of interest.

Here, X represents a protected or non-protected carboxyl group. The carboxyl group may be an unprotected carboxyl group, or may be a free acid or may configure a salt. The protecting group of the carboxyl group is as described above. The protection and deprotection of the carboxyl group can be appropriately carried out by ordinary methods in organic chemistry according to the objective. For example, in one aspect of the present invention, in terms of preventing the carboxyl group from reacting during the manufacturing method of the present invention, it is preferred that the carboxyl group is protected. On the other hand, in one aspect of the present invention, in terms of requiring rapid reaction as the substrate for aminoacylase, it is also desirable to deprotect the protected carboxyl group before the hydrolysis reaction by the enzyme since it is possible that the enzyme reaction rate will be reduced due to a protecting group being bound to the carboxyl group.

Acyl indicates an acyl group. An acyl group can also be represented as R—CO—. R is a hydrogen atom, a linear or branched alkyl group, and the like, and may be substituted by one or more substituents. Examples of an alkyl group as R can be an alkyl group having 1-3 carbons, preferably 1-2 carbons. Moreover, the substituent for R may be any substituent that may be a substituent of an alkyl group as long as it does not inhibit reactions in the manufacturing method of the present invention, and for example may be a halogen atom such as a chlorine or fluorine atom, a hydroxyl group, a substituted or non-substituted phenyl group, and the like. Examples of an acyl group represented by R—CO— include an acetyl group, a hydroxyacetyl group, a chloroacetyl group, a trifluoroacetyl group, a formyl group, a propionyl group, a benzoyl group, and the like. For example, in one aspect of the present invention, in terms of requiring rapid reaction as the substrate for aminoacylase, an acetyl group, a benzoyl group, and the like are preferred.

$R^1$ indicates the substituent moiety bound to the β carbon atom among side chain substituents that configure amino acids (except when it is a hydrogen atom). $R^1$ may possess a functional group, and the functional group may be protected. The protection and deprotection of the functional group may also be appropriately carried out in the manufacturing method of the present invention. For example, the functional group comprised in $R^1$ may be protected/deprotected simultaneously with the protection and deprotection of the amino group or carboxyl group, or a step of independently protecting/deprotecting the functional group comprised in $R^1$ separately with the protection and deprotection of other substituents may also be set up. Examples of $R^1$ are a linear or branched alkyl group, an aromatic substituent, and the like, and these may be substituted. The substituent may be a substituent etc. known to be present in the amino acid side chain, and may be a hydroxyl group, a —CO—$NH_2$ group, a carboxyl group, an amino group, a —NH—$C(NH_2)_2$ group, a thiol group, an alkylthio group, and the like, the substituent of which may be a free acid or base, or a salt thereof. Moreover, the alkyl group can be e.g. an alkyl group having 1-6 carbons, preferably 1-5 carbons, and the aromatic substituent can be an aryl group such as a phenyl group, as well as a heteroaryl group such as an indolyl group and an imidazoyl group.

In one aspect of the present invention, in terms of providing a β-thioamino acid derivative that can be employed as the linking site for NCL for synthesizing a natural protein, it is preferred that in the above formula, said substituent $R^1$ is the substituent moiety bound to the β carbon atom of an amino acid selected from the group consisting of Arg, Asn, Asp, Glu, Gln, His, Leu, Lys, Met, Phe, Trp, and Tyr (provided that it is not a hydrogen atom). Moreover, it is preferred from a similar perspective that said substituent $R^2$ is a protecting group for the thiol group, examples of which include a PMB (para-methoxybenzyl) group, an Acm (acetamidomethyl) group, a benzyl group, a Trt (trityl) group, a disulfide group, a t-butyl group, and the like. Moreover, in terms of the substrate of a reaction by a hydrolase, it is preferred that, in the above formula, Acyl is an acetyl group and X is a carboxyl group and the carboxyl group may be a free acid or may be a salt.

In one aspect of the present invention, the β-thioamino acid derivative of the present invention can be efficiently manufactured by a manufacturing method via an amino acid derivative possessing a leaving group at the β-position.

Moreover, as one aspect of the present invention, as a result of extensive investigations in order to enable manufacture of a β-thioamino acid derivative possessing substituent $R^1$ at the β carbon atom, the present inventors found as one aspect that with a β-thioamino acid derivative of an amino acid possessing an aromatic substituent as substituent $R^1$ at the β-position, an amino acid derivative possessing a leaving group L at the β-position can be efficiently manufactured by a method of introducing a halogen atom at the β-position utilizing photoreaction.

Natural amino acids possessing an aromatic substituent as substituent $R^1$ at the β-position include phenylalanine, tyrosine, tryptophan, and histidine. Moreover, the amino acid possessing an aromatic substituent as substituent $R^1$ at the β-position may be non-natural. The aromatic substituent may be an aryl group or a heteroaryl group, and for example may be an aryl group such as a phenyl group and a naphthyl group, or a heteroaryl group such as imidazole, pyrrole, and thiazole groups.

In this method, an amino acid possessing an aromatic substituent as substituent $R^1$ at the β-position can be the raw material. For example, as natural examples, phenylalanine, tyrosine, tryptophan, and histidine can be the raw material. Those that are commercially available may be employed as these aromatic amino acids as the raw material, or they may be prepared by well-known methods. These amino acids may be employed as an amino acid as a mixture with D- and L-forms for the α carbon atom or as an optically active form consisting substantially of only one of D- or L-form for the α carbon atom, depending on the ease of availability and other circumstances. In one aspect of the present invention, an amino acid as an equal mixture of D- and L-forms for the α carbon atom may be employed as the raw material, which in this case can be expressed as employing a racemic amino acid as the raw material. When these racemic amino acids are employed as the raw material, because the reaction proceeds as a racemate per se and the intermediate composition is also obtained as a racemate, the crystallization efficiency of the intermediate composition is high and purification is facilitated. Moreover, when an optically active form is employed as the raw material, the reaction can be proceeded without being concerned about producing racemization, without controlling the configuration regarding the α asymmetric carbon atom. In one aspect of the present invention, in terms of efficiently carrying out purification of the intermediate composition, it is preferred to employ a racemic amino acid with high crystallization efficiency as the raw material compound.

The method of introducing a halogen atom by photoreaction can be carried out by well-known methods. In general, it can be carried out by reacting a halogenating reagent in a solvent under exposure to light. For example, it is carried out in carbon tetrachloride employing N-bromosuccinimide (NBS) as the brominating reagent and reacting under exposure to a 200 W lamp for 1 hour. N-bromosuccinimide and the like can be employed as the halogenating reagent, and in one aspect of the present invention N-bromosuccinimide is preferred. Moreover, the reaction time is not particularly limited as long as the halogenating reaction is allowed to sufficiently proceed, and for example can be 30 minutes-2 hours, preferably 1 hour. Moreover, in terms of efficiently carrying out the photoreaction, the experiment system may be covered with e.g. aluminum foil.

In other words, this method can be said to be one aspect of carrying out "a step of manufacturing an amino acid derivative possessing substituent $R^1$ and a leaving group L on the β carbon atom" as step (P) before the introduction reaction of a thiol group as reaction (A) in said step (I) in the manufacturing method of the present invention. Moreover, particularly when substituent $R^1$ is an aromatic substituent, it can be carried out as "a step of introducing a leaving group L at the β carbon atom of an amino acid derivative possessing substituent $R^1$ on the β carbon atom," and this step can be referred to herein as (P-1) for convenience. In this case, the introduced leaving group L is subjected to introduction of a thiol group simultaneously with the detachment of the leaving group L upon the introduction reaction of a thiol group as reaction (A).

Depending on the extent of reactivity etc. of the substrate, (B) the reaction of converting the carboxyl group or amino group in order to allow it to be the substrate of the enzyme in step (I) may be carried out before the step of manufacturing an amino acid derivative possessing a leaving group L at the β-position as the above step (P), or it may be carried out after the step. If the structure to be the substrate of the enzyme reaction has a structure that has high reactivity in other steps as well, it is preferred to manufacture an amino acid derivative possessing a leaving group L at the β-position, protect it to be a protecting group during the reaction of introducing a thiol group at the β-position, and then carrying out a conversion reaction in order to allow it to be the substrate of the enzyme reaction.

Further, as one aspect of the present invention, as a result of extensive investigations in order to enable manufacture of a β-thioamino acid derivative possessing various substituent $R^1$ not limited to aromatic substituents, the present inventors found as one aspect that by employing a method of reacting glycine as the raw material with an aldehyde compound represented by $R^1CHO$, an amino acid derivative possessing $R^1$ group of various structures at the β-position and possessing a hydroxyl group as the leaving group L at the β-position can be efficiently manufactured. According to this method, various amino acids possessing various structures not limited to aromatic amino acids can also be manufactured by employing an aldehyde corresponding to the structure of the compound of interest.

By reacting glycine with an aldehyde compound represented by $R^1CHO$, a covalent bond is formed between the α carbon atom of glycine and the carbon atom configuring the aldehyde group of an aldehyde compound represented by $R^1CHO$. As a result, in the compound produced by this reaction, the carbon atom that had configured the aldehyde group will correspond to the β carbon atom of the amino acid, and an amino acid derivative possessing substituent $R^1$, a hydroxyl group, and a hydrogen atom at the β carbon atom is produced.

Accordingly, by employing this method, as compared to a natural or non-natural amino acid possessing two hydrogen atoms at the β carbon atom, an amino acid derivative possessing a protected or non-protected thiol group instead of one of the hydrogen atoms bound to the β carbon atom can be manufactured.

For example, in terms of manufacturing an amino acid derivative having a protected or non-protected thiol group introduced at the β-position of a natural amino acid, an amino acid derivative having a protected or non-protected thiol group introduced at the β-position of an amino acid selected from the group consisting of Arg. Asn. Asp, Glu. Gin, His. Leu, Lys, Met, Phe, Trp, and Tyr as the amino acid possessing two hydrogen atoms at the β carbon atom can be manufactured.

Examples were described with natural amino acids, but manufacture can be similarly carried out even for a non-natural amino acid if is an amino acid possessing two hydrogen atoms at the β carbon atom.

This method of reacting glycine with an aldehyde, for example when manufacturing phenylalanine by this method, can be carried out by a method of condensing glycine and benzaldehyde under strong basic condition. For example, a strong basic aqueous solution can be employed as the solvent, and preferably 5 N NaOH and the like can be employed. The temperature can be from low temperature to about room temperature, preferably 0-40° C. and more preferably about 10-20° C. The reaction time can be 30 minutes-3 hours, preferably 1 hour. This method can be carried out with reference to e.g. the method of Nakagawa H et al, Chem. Pharm. Bull. 2003, 51, 1363-1367.

The aldehyde compound represented by $R^1CHO$ employed in this method can be determined according to the structure of the amino acid derivative of interest.

According to a method of manufacturing an amino acid derivative possessing a hydroxyl group at the β-position with glycine as the raw material, glycine as the raw material is not an asymmetric carbon atom because it has a structure of two hydrogen atoms bound to the α carbon atom. By carrying out the above reaction with this glycine as the raw material, an amino acid derivative possessing a hydroxyl group at the β-position can ordinarily be obtained as a racemate.

In other words, this method can be said to be one aspect of carrying out "a step of manufacturing an amino acid derivative possessing substituent $R^1$ and a leaving group L on the β carbon atom" as step (P) before the introduction reaction of a thiol group as reaction (A) in said step (I) in the manufacturing method of the present invention. Moreover, in particular, the step of reacting glycine with an aldehyde compound represented by $R^1CHO$ can be referred to herein as step (P-2) for convenience.

An amino acid derivative possessing a hydroxyl group at the β-position can be obtained by this method. This amino acid derivative possessing a hydroxyl group at the β-position, similarly to a compound obtained by the method of (P-1) described above, can be converted into an amino acid derivative possessing a protected or non-protected thiol group at the β-position by a reaction of detaching the leaving group at the β-position and introducing a thiol group at the β-position. In this case, for the leaving group at the β-position, the hydroxyl group per se may be the leaving group, but the hydroxyl group may be converted into a substituent that is more easily detachable and then detached. In other words, a step of converting a hydroxyl group into a leaving group may be further included. For example, the hydroxyl group can be more easily detached by mesylating it to be a MsO group. In this case. MsO will be the leaving group. Such a step of converting a hydroxyl group into a leaving group can be carried out by a method of reacting the hydroxyl group with mesyl chloride, tosyl chloride, trifluoromethanesulfonic anhydride, and the like. By these reactions, the leaving group will become MsO, TsO, and TfO groups, respectively.

In this way, an amino acid derivative possessing a leaving group at the β-position can also be manufactured by a method of using glycine as the raw material.

When the manufacturing method of the present invention is carried out with an aromatic amino acid or glycine as a racemate as the raw material, the raw material compound in this step of introducing a thiol group is an equal mixture of D- and L-forms for the α carbon atom, which can also be referred to as a racemic amino acid. Moreover, when an optically active aromatic amino acid is employed as the raw material, since it is possible that the reaction can be carried out without controlling stereoisomerism also in the step of introducing a thiol group at the β-position and racemization is allowed to proceed to an extent, it is possible that the raw material compound in the step of introducing a thiol group is a mixture of D- and L-forms.

In one aspect of the manufacturing method of the present invention, when it is via an amino acid derivative possessing a leaving group at the β-position, a step of introducing a thiol group at the β-position can be carried out after the above reaction. The step of introducing a thiol group at the β-position is as described above.

Further, as one example of a method of using glycine as the raw material, a method of reacting glycine with a ketone compound can be employed in addition to a method of reacting glycine with an aldehyde compound as described above. This method is useful as a method of manufacturing an amino acid having a protected or non-protected thiol group introduced at the β-position of an amino acid having one hydrogen atom and two substituted or non-substituted alkyl groups bound to the β carbon atom.

For example, in terms of manufacturing an amino acid derivative having a protected or non-protected thiol group introduced at the β-position of a natural amino acid, an amino acid derivative having a protected or non-protected thiol group introduced at the β-position of an amino acid selected from the group consisting of Val and Ile as the amino acid possessing one hydrogen atom at the β carbon atom can be manufactured.

Examples were described with natural amino acids, but manufacture can be similarly carried out even for a non-natural amino acid if it is an amino acid possessing one hydrogen atom at the β carbon atom.

This method of reacting glycine with a ketone can be carried out for example according to the reaction of condensing glycine and an aldehyde as described above. For example, it can be carried out by a method of e.g. condensing glycine and acetone under strong basic condition at a low temperature.

The ketone compound employed in this method can be determined according to the structure of the amino acid derivative of interest. When the amino acid derivative of interest is a compound possessing substituent $R^3$ in addition to substituent $R^1$ at the β carbon atom, it can be carried out by employing a ketone compound represented by $R^1$—(C=O)—$R^3$. Here, $R^1$ and $R^3$ indicate a substituted or non-substituted alkyl group. Examples of an alkyl group can be an alkyl group having 1-6 carbons such as a methyl group, an ethyl group, a propyl group, and the like. The substituent may be various substituents that may exist in the amino acid side chain, and these may be protected.

By reacting glycine with a ketone compound represented by $R^1$—(C=O)—$R^3$, a double bond is formed between the α carbon atom of glycine and the carbon atom configuring the ketone group of the ketone compound represented by $R^1$—(C=O)—$R^3$, and the carbonyl oxygen that had configured the ketone group is detached. As a result, in the compound produced by this reaction, the carbon atom that had configured the ketone group will correspond to the β carbon atom of the amino acid, and an amino acid derivative possessing substituent $R^1$ and substituent $R^3$ at the β carbon atom is produced. By adding a protected or non-protected thiol group to the β carbon atom and a hydrogen atom to the α carbon atom to the double bond between the α and β carbon atoms produced in this reaction, a protected or non-protected thiol group can be introduced at the β carbon atom.

The reaction of adding a thiol group to the β carbon atom in this case can be carried out by well-known methods. For example, it can be carried out by a method of carrying out a nucleophilic reaction of a thiol compound in an organic solvent such as DMF with a base such as diazabicycloundecene (DBU).

This method, with the manufacture of an amino acid derivative possessing a thiol group at the β-position of a natural valine as an example, can be represented as the following chemical reaction formula.

[Chemical Formula 7]

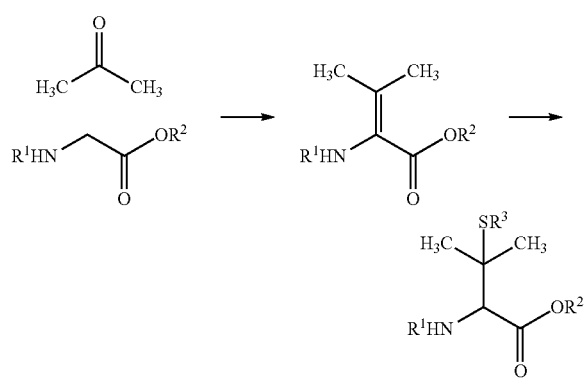

Further, as an amino acid possessing a thiol group in the side chain, an amino acid derivative possessing a thiol group at the γ-position can also be manufactured.

As one example of a method of using glycine as the raw material, an amino acid derivative possessing a hydroxyl group at the β-position and a thiol group at the γ-position can be manufactured by a method of reacting glycine with an aldehyde possessing a thiol group at the α-position.

This method, with the manufacture of an amino acid derivative possessing a thiol group at the γ-position of a natural threonine as an example, can be represented as the following chemical reaction formula.

[Chemical Formula 8]

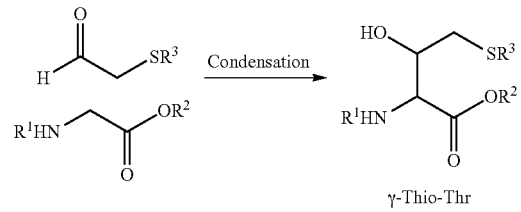

γ-Thio-Thr

As one example of a method of using glycine as the raw material, an amino acid derivative possessing an alkyl group at the β-position and a thiol group at the γ-position can be manufactured by a method of reacting glycine with a ketone possessing a thiol group at the α-position.

This method, with the manufacture of an amino acid derivative possessing a thiol group at the γ-position of a natural valine as an example, can be represented as the following chemical reaction formula.

[Chemical Formula 9]

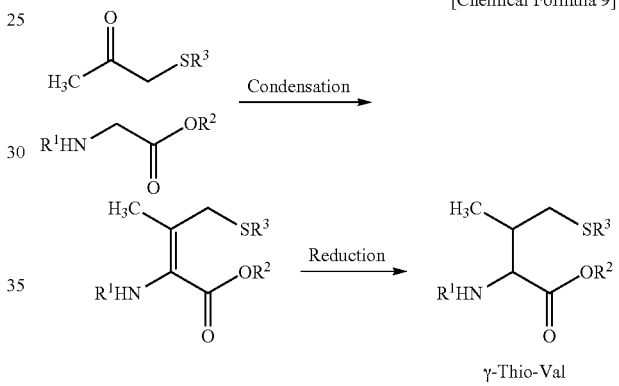

γ-Thio-Val

As shown above, by applying a method of reacting glycine with an aldehyde compound and a method of reacting glycine with a ketone compound, an amino acid derivative possessing a thiol group at the γ-position can be manufactured as shown above.

These methods are useful as methods of manufacturing an amino acid having a protected or non-protected thiol group introduced at the γ-position of an amino acid having one hydroxyl group bound to the β carbon atom.

The optically active D- or L-amino acid derivative possessing a thiol group in the side chain obtained by the method of the present invention can be employed for various applications directly as an amino acid derivative, or can be employed for synthesizing a D- or L-protein, depending on the objective. In particular, it can be employed as the linking site in NCL for manufacturing these proteins. In particular, an amino acid derivative possessing a thiol group at the β-position can be favorably employed, but an amino acid derivative possessing a thiol group at the γ-position can similarly be favorably employed. The carboxyl group, amino group, thiol group, other side chain substituents, and the like of the amino acid derivative obtained by the method of the present invention can be protected or deprotected and employed according to the objective/application thereof. For example, only one of carboxyl or amino group can be deprotected and employed for peptide solid phase synthesis and the like. Moreover, the amino acid derivative possessing a protected thiol group in the side chain obtained by the method of the present invention is useful in that peptide synthesis can be carried out with the thiol group still protected by a protecting group, and then carrying out a NCL linking reaction. Moreover, if a method of removing the thiol group moiety after the NCL linking reaction is employed, an amino acid that was not allowed to be the NCL linking site according to the conventional method could also be the NCL linking site, and is thus useful for D- or L-protein synthesis.

Note that the terms used herein are to be employed to describe particular embodiments and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

Terms such as first and second are sometimes employed to express various elements, and it should be recognized that these elements are not to be limited by these terms. These terms are employed solely for the purpose of discriminating one element from another, and it is for example possible to describe a first element as a second element, and similarly, to describe a second element as a first element without departing from the scope of the present invention.

The present invention will now be more specifically described by Examples. However, the present invention can be embodied by various embodiments, shall not be construed as being limited to the Examples described herein.

EXAMPLES

Synthesis of an Optically Active Aromatic Amino Acid Derivative Possessing a Thiol Group at the β-Position with an Aromatic Amino Acid as the Starting Material As represented in the following reaction formula, the synthesis reaction of D,L-phenylalanine possessing a thiol group at the β-position was carried out with an aromatic amino acid as the starting material. Compound numbers indicated after compound names in Synthesis Examples indicate compound numbers indicated in the following reaction formula.

[Chemical Formula 10]

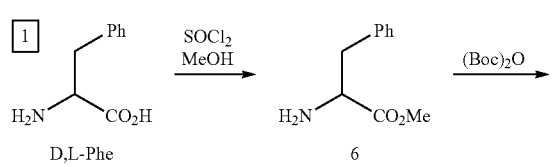

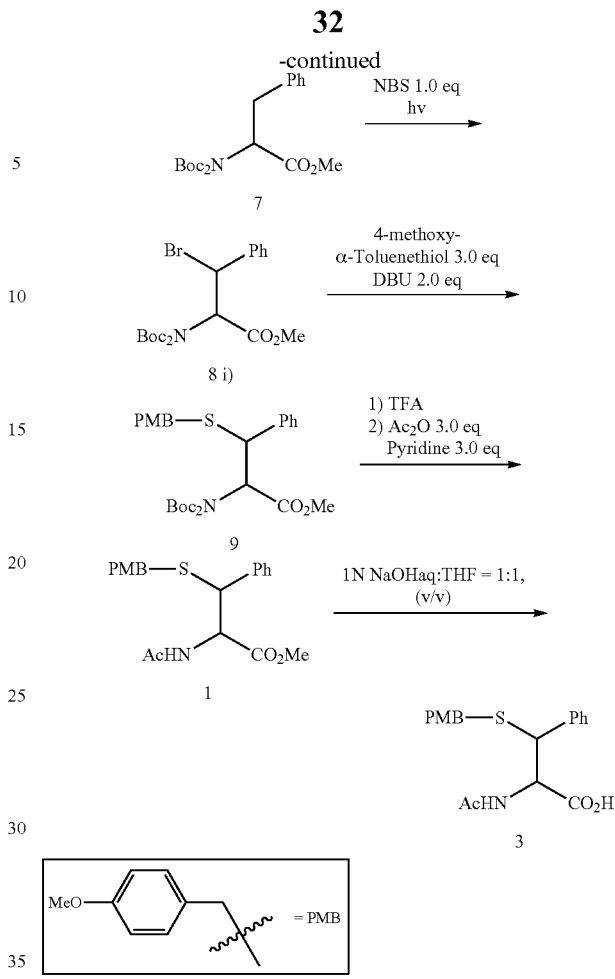

i) D. Crich, A. Banerjee, *J. Org. Chem.*, 2006, 71, 7106-7109

Synthesis Example 1

D,L-phenylalanine methyl ester hydrochloride (Compound 6)

In the presence of argon, D,L-phenylalanine (10.0 g, 60.5 mmol) was added to methanol (48.4 mL), the solution was cooled to 0° C., and then thionyl chloride (4.8 ml, 66.6 mmol) was added dropwise. This was then stirred under reflux for 1 hour. The reaction solution was concentrated under reduced pressure, and then recrystallization was carried out with a mixed solvent of 5 ml methanol and 80 mL diethyl ether to obtain D,L-phenylalanine methyl ester hydrochloride (Compound 6) (11.8 g).

Synthesis Example 2

N,N-DiBoc-D,L-phenylalanine-methyl ester (Compound 7)

Compound 6 (11.8 g) was suspended in THF (292 mL), then cooled to 0° C., to which $Na_2CO_3$ (7.0 g, 1.0 eq.) dissolved in water (164 mL) was added. Then, $(Boc)_2O$ (28.7 g, 2.0 eq.) was added dropwise, and this was stirred at ordinary temperature for 2 hours. The compound produced by the reaction was extracted with ethyl acetate, and then washed with saturated ammonium chloride aqueous solution, water, and saturated saline. The organic layer was dried with magnesium sulfate, filtered, and concentrated under reduced pressure to obtain a crude product of N-Boc-D,L-phenylalanine-methyl ester.

This crude product was further dissolved in acetonitrile (202 mL), 4-dimethylaminopyridine (DMAP) (7.4 g, 1.0 eq.) was added as a catalyst, then (Boc)$_2$O (39.6 g, 3.0 eq.) was added, and this was stirred at room temperature for 12 hours. This was then concentrated under reduced pressure, extracted with ethyl acetate, and washed with saturated ammonium chloride aqueous solution, water, and saturated saline. The organic layer was dried with magnesium sulfate, filtered, and concentrated under reduced pressure. Compound 7 (19.8 g) was then purified by silica gel column chromatography with a developing solvent of ethyl acetate:hexane=1:3.

Synthesis Example 3

N,N-DiBoc-β-bromo-D,L-phenylalanine-methyl ester (Compound 8)

In the presence of argon, Compound 7 (5.0 g, 13.2 mmol) was dissolved in carbon tetrachloride (264 mL), N-bromosuccinimide (2.3 g, 1.0 eq.) was added, and this was then reacted under reflux for 1 hour under exposure to light by a 200 W incandescent lamp. The experiment system was covered with aluminum foil in order to intensify the light. Subsequently, after the reaction, this was cooled to room temperature, and succinimide was removed by filtration. This was further concentrated under reduced pressure to obtain Compound 8 (5.7 g).

$C_{20}H_{28}BrNO_6[M+Na]^+$: Cal 480.00. Found 480.16.
$^1$HNMR (400 MHz) δ: 7.55-7.24 (m, 5H), 5.76 (d, 1H), 5.74 (d, 1H), 5.68 (d, 1H), 5.61 (d, 1H), 3.80 (s, 3H), 3.59 (s, 3H), 1.58 (s, 9H), 1.38 (s, 9H)

Synthesis Example 4

N,N-DiBoc-β-methoxybenzylmercapto-D,L-phenylalanine-methyl ester (Compound 9)

To a solution of Compound 8 (1.27 g, 2.78 mmol) in DMF (7.9 mL), a DMF solution (4 mL) of DBU (1.9 mL, 9.7 mmol) salt of 4-methoxy-α-toluenethiol (1.5 mL, 12.5 mmol) was added dropwise in the presence of argon at room temperature for 3 hours. The compound produced by the reaction then was extracted with ethyl acetate, and washed with saturated ammonium chloride aqueous solution, water, and saturated saline. The organic layer was dried with magnesium sulfate, filtered, and concentrated under reduced pressure. Compound 9 (1.0 g) was purified by silica gel column chromatography with a developing solvent of ethyl acetate:hexane=1:7.

Synthesis Example 5

N-Acetyl-β-methoxybenzylmercapto-D,L-phenylalanine-methyl ester (Compound 1)

Compound 9 (2.4 g, 4.6 mmol) was dissolved in DCM (46 mL), an equal amount of TFA was added, this was reacted at room temperature for 5 minutes, followed by concentration under reduced pressure and azeotroping with toluene. This was then dissolved in DCM (46 mL), pyridine (1.1 ml, 13.8 mmol) and Ac$_2$O (1.2 ml, 13.8 mmol) were added, and reacted at room temperature for 30 minutes. After the reaction, a small amount of methanol was added to stop the reaction, and concentrated under reduced pressure to obtain Compound 1 (1.1 g).

$C_{18}H_{21}NO_3S [M+H]^+$: Cal 332.12. Found 331.13.

Synthesis Example 6

N-Acetyl-β-methoxybenzylmercapto-D,L-phenylalanine (Compound 3)

Compound 1 (1.0 g) was dissolved in THF (5.5 mL), 1 N NaOH (5.5 mL) was added at room temperature, and reacted for 30 minutes. Subsequently, the reaction system was acidified to pH 2-3 with 1 N HCl, and then extracted three times with ethyl acetate. The organic layer was dried with magnesium sulfate, filtered, and concentrated under reduced pressure. The crude product obtained was further recrystallized by ethyl acetate to obtain Compound 3 (0.65 g).

$^1$HNMR (400 MHz) δ: 7.40-7.22 (m, 5H), 7.40-7.22 (m, 5H), 7.12 (d, 2H), 7.07 (d, 2H), 6.82 (d, 2H), 6.80 (d, 2H), 4.96 (d, 1H), 4.85 (d, 1H), 4.23 (d, 1H), 4.10 (d, 1H), 3.77 (s, 3H), 3.76 (s, 3H), 3.54 (q, 2H), 3.47 (q, 2H), 1.96 (s, 3H), 1.80 (s, 3H)

Manufacture of an Optically Active Amino Acid Derivative from a D,L-Amino Acid Derivative Possessing a Thiol Group at the β-Position As represented in the following reaction formula, an enzyme was allowed to act on a D,L-amino acid derivative possessing a thiol group at the β-position to carry out the synthesis reaction of an optically active amino acid derivative possessing a thiol group at the β-position. Compound numbers indicated after compound names in Synthesis Examples indicate compound numbers indicated in the following reaction formula.

[Chemical Formula 11]

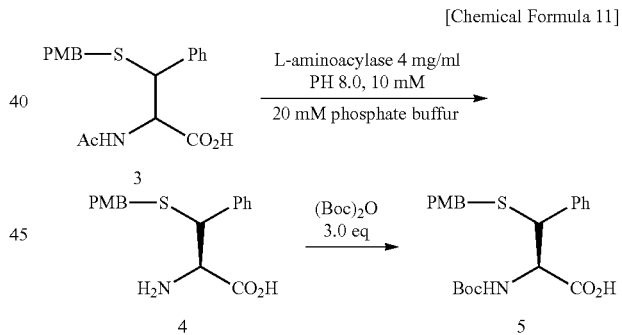

Synthesis Example 7-1

N-Boc-β-methoxybenzylmercapto-L-phenylalanine (Compound 5)

Compound 3 (100 mg, 0.28 mmol) was dissolved in phosphate buffer (pH 8.0, 14 mL), and then a phosphate buffer solution (pH 8.0, 14 mL) of L-aminoacylase (from *Aspergillus* spp.) (111 mg, 30 U/mg; product name acylase "Amano" from Amano Enzyme Inc.) was added, and this was reacted at 37° C. for 2 days. Then, at room temperature, a THF (28 mL) solution of Boc$_2$O (3.0 eq.) was added to the reaction system, and this was reacted for 1 hour to carry out Boc protection. Subsequently, the reaction system was acidified to pH 2-3 with 1 N HCl, and then extracted three times with ethyl acetate. The organic layer was dried with magnesium sulfate, filtered, and concentrated under reduced pressure. Compound 5 was purified by silica gel column chromatography with a developing solvent of 1% formic acid-containing ethyl acetate to obtain Compound 5 at an isolated yield of 39%.

$C_{22}H_{27}NO_5S$ [M+Na]$^+$: Cal 440.15. Found 440.18.

Moreover, in Synthesis Example 7, N-Acetyl-β-methoxybenzylmercapto-D,L-phenylalanine that was not degraded with L-aminoacylase was similarly purified with purification by silica gel column chromatography in Synthesis Example 7, and this was obtained at 50% yield (50 mg). This will be the raw material for synthesizing N-Boc-β-methoxybenzylmercapto-D-phenylalanine by employing D-aminoacylase.

Synthesis Example 7-2

N-Boc-β-methoxybenzylmercapto-D-phenylalanine

Moreover, in the above Synthesis Example 7, by carrying out synthesis with a similar method except that L-aminoacylase was replaced with D-aminoacylase, N-Boc-β-methoxybenzylmercapto-D-phenylalanine was also synthesized.

$C_{22}H_{27}NO_5S$ [M+Na]$^+$: Cal 440.15. Found 440.18.

From the above Synthesis Examples, by using an aromatic amino acid as the raw material, introducing a protected thiol group at the β-position, and employing an aminoacylase selective for L-forms and a D-selective aminoacylase, respectively, a L-amino acid possessing a protected thiol group at the β-position and a D-amino acid possessing a protected thiol group at the β-position could each be easily and efficiently obtained. With the conventional method. L-amino acid was used as the raw material and the stereoisomerization of the α-position was suppressed, or isomerized D-form was often separated, which lead to not only difficulty in improvement of yield but also complication of industrial production. In contrast, according to the present invention, the aforementioned caution is unnecessary by using a mixed D,L-amino acid as the raw material or the intermediate. Moreover, because a mixed D,L-amino acid has high crystallization efficiency and is easy to purify, a drastic reduction of process can be realized. The technology of the present invention is a method that enables practical application of a non-natural amino acid possessing a thiol group at the β-position that can be utilized in NCL to industrial production.

As represented in the following reaction formula, the synthesis reaction of a D,L-tyrosine possessing a thiol group at the β-position was carried out with an aromatic amino acid as the starting material. Compound numbers indicated after compound names in Synthesis Examples indicate compound numbers indicated in the following reaction formula.

Synthetic route of a tyrosine derivative possessing a thiol at the b-position

[Chemical Formula 12]

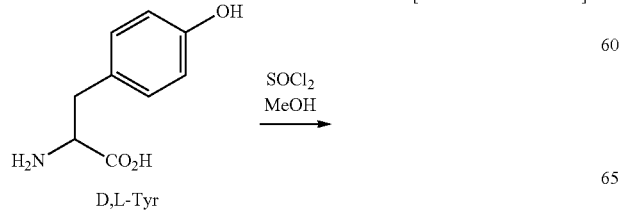

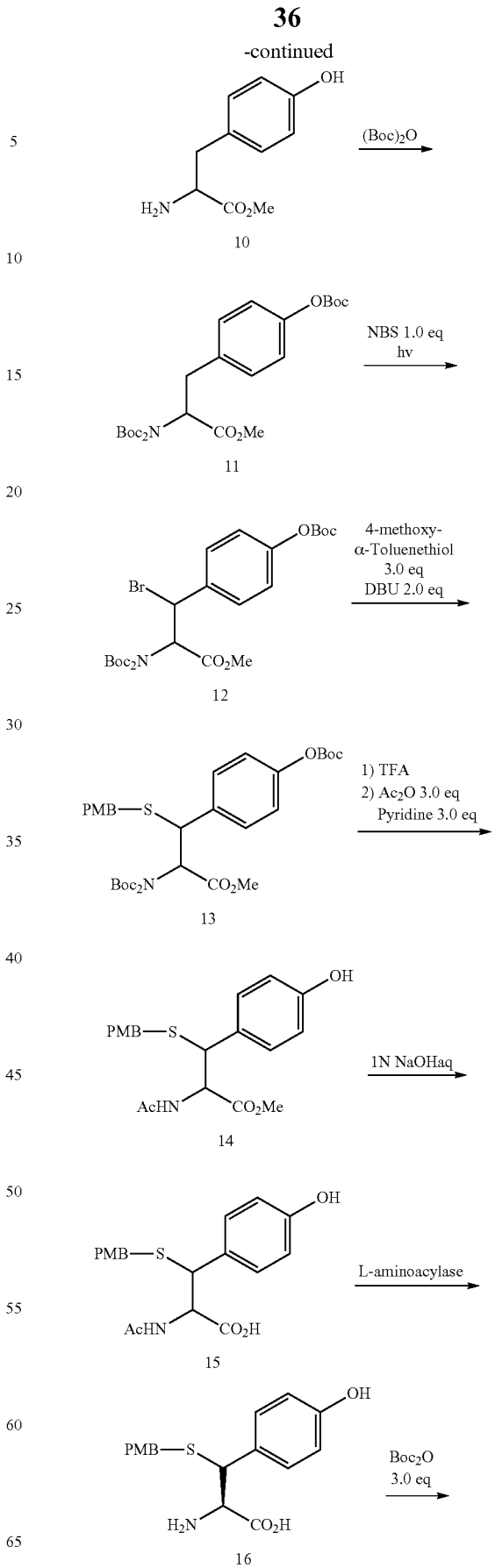

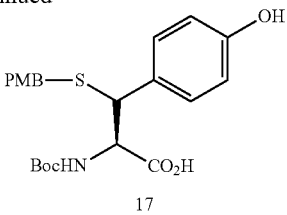

17

Synthesis Example 8

D,L-tyrosine methyl ester hydrochloride (Compound 10)

In the presence of argon, D,L-tyrosine (10.0 g, 55.1 mmol) was added to methanol (88 mL), the solution was cooled to 0° C., and then thionyl chloride (3.97 ml, 60.6 mmol) was added dropwise. This was then stirred under reflux for 1 hour. The reaction solution was concentrated under reduced pressure, and then recrystallization was carried out with a mixed solvent of 5 mL methanol and 80 mL diethyl ether to obtain Compound 10 (10.8 g).

Synthesis Example 9

N,N-DiBoc-O-Boc-D,L-tyrosine-methyl ester (Compound 11)

Compound 10 (10.8 g) was suspended in THF (184 mL), then cooled to 0° C., to which $Na_2CO_3$ (5.9 g, 1.0 eq.) dissolved in water (92 mL) was added. Then, $(Boc)_2O$ (24 g, 2.0 eq.) was added dropwise, and this was stirred at ordinary temperature for 2 hours. This was extracted with ethyl acetate, and then washed with saturated ammonium chloride aqueous solution, water, and saturated saline. The organic layer was dried with magnesium sulfate, filtered, and concentrated under reduced pressure to obtain a crude product of N-Boc-D,L-tyrosine-methyl ester. This product was dissolved in acetonitrile (184 mL), DMAP (6.7 g, 1.0 eq.) was added, then $(Boc)_2O$ (36.2 g, 3.0 eq.) was added, and this was stirred for 12 hours. This was then concentrated under reduced pressure, extracted with ethyl acetate, and washed with saturated ammonium chloride aqueous solution, water, and saturated saline. The organic layer was dried with magnesium sulfate, filtered, and concentrated under reduced pressure. Compound 11 (22.9 g) was purified by silica gel column chromatography with a developing solvent of ethyl acetate:hexane=1:3.

$^1$HNMR (400 MHz) δ: 7.28-7.04 (m, 5H), 5.15 (dd, 1H), 3.43 (dd, 1H), 3.20 (dd, 1H), 1.55 (s, 9H), 1.40 (s, 18H)

Synthesis Example 10

N,N-DiBoc-β-bromo-O-Boc-D,L-tyrosine-methyl ester (Compound 12)

In the presence of argon, Compound 11 (6.0 g, 12 mmol) was dissolved in carbon tetrachloride (120 mL), N-bromosuccinimide (2.1 g, 1.0 eq.) was added, and this was then reacted under reflux for 1 hour under exposure to light by a 200 W incandescent lamp. The experiment system was covered with aluminum foil in order to intensify the light. After the reaction, this was cooled to room temperature, and succinimide was removed by filtration. This was further concentrated under reduced pressure to obtain Compound 12 (6.6 g).

Synthesis Example 11

N,N-DiBoc-β-methoxybenzylmercapto-O-Boc-D,L-tyrosine-methyl ester (13)

To a solution of Compound 12 (2.9 g, 5.1 mmol) in DMF (23 mL), a DMF solution (11.5 mL) of DBU (1.5 mL, 10.2 mmol) salt of 4-methoxy-α-toluenethiol (1.4 mL, 10.2 mmol) was added dropwise in the presence of argon at room temperature, and reacted for 3 hours. This was then extracted with ethyl acetate, and washed with saturated ammonium chloride aqueous solution, water, and saturated saline. The organic layer was dried with magnesium sulfate, filtered, and concentrated under reduced pressure. Compound 13 (1.2 g) was purified by silica gel column chromatography with a developing solvent of ethyl acetate:hexane=1:7.

Synthesis Example 12

N-Acetyl-β-methoxybenzylmercapto-D,L-tyrosine-methyl ester (Compound 14)

Compound 13 (1.3 g, 2.1 mmol) was dissolved in DCM (21 mL), an equal amount of TFA was added, this was reacted at room temperature for 5 minutes, followed by concentration under reduced pressure and azeotroping with toluene. This was then dissolved in DCM (21 mL), pyridine (0.8 ml, 10.5 mmol) and $Ac_2O$ (0.9 ml, 10.5 mmol) were added, and reacted at room temperature for 30 minutes. After the reaction, a small amount of methanol was added to stop the reaction, and concentrated under reduced pressure to obtain Compound 14 as a crude product (441 mg).

$C_{18}H_{22}NO_4S$ $[M+H]^+$: Cal 348.12. Found 348.17.

Synthesis Example 13

N-Acetyl-β-methoxybenzylmercapto-D,L-tyrosine (Compound 15)

Crude product 14 (441 mg) was dissolved in THF (10.5 mL), 1 N NaOH (10.5 mL) was added at room temperature, and reacted for 30 minutes. Subsequently, the reaction system was acidified to pH 2-3 with 1 N HCl, and then extracted three times with ethyl acetate. The organic layer was dried with magnesium sulfate, filtered, and concentrated under reduced pressure. Compound 15 (301 mg) was purified by silica gel column chromatography with a developing solvent of 1% formic acid-containing ethyl acetate:hexane=1:2.

Synthesis Example 14-1

N-Boc-β-methoxybenzylmercapto-L-tyrosine (Compound 17)

Compound 15 (72 mg, 0.19 mmol) was dissolved in phosphate buffer (pH 8.0, 9 mL), and then a phosphate buffer solution (pH 8.0, 10 mL) of L-aminoacylase (from *Aspergillus* spp.) (111 mg, 30 U/mg; product name acylase "Amano" from Amano Enzyme Inc.) was added, and this was reacted at 37° C. for two days. Then, at room temperature, a THF (19 mL) solution of $Boc_2O$ (124 mg, 3.0 eq.) was added to the reaction system, and this was reacted for 1 hour to carry out Boc protection. Subsequently, the reaction system was acidified to pH 2-3 with 1 N HCl, and then extracted three times with ethyl acetate. The organic layer was dried with magnesium sulfate, filtered, and concentrated under reduced pressure. Compound 17 was obtained at 29 mg by silica gel column chromatography with a developing solvent of 1% formic acid-containing ethyl acetate:hexane=4:1.

Synthesis Example 14-2

N-Boc-β-methoxybenzylmercapto-D-tyrosine

Moreover, in the above Synthesis Example 14-1, by carrying out synthesis with a similar method except that L-aminoacylase was replaced with D-aminoacylase, N-Boc-β-methoxybenzylmercapto-D-tyrosine was also synthesized.

$C_{22}H_{27}NO_5S$ [M+Na]$^+$: Cal 440.15. Found 440.18.

From the above Synthesis Example, by using an aromatic amino acid as the raw material, introducing a protected thiol group at the β-position, and employing an aminoacylase selective for L-forms, a L-tyrosine derivative possessing a protected thiol group at the β-position and a D-amino acid possessing a protected thiol group at the β-position could each be easily and efficiently obtained.

Manufacture of Various Optically Active Amino Acid Derivatives Possessing a Thiol Group at the β-Position with Glycine as the Starting Material As represented in the following reaction formula, the synthesis reaction was carried out with glycine as the starting material. Compound numbers indicated after compound names in Synthesis Examples indicate compound numbers indicated in the following reaction formula.

[Chemical Formula 13]

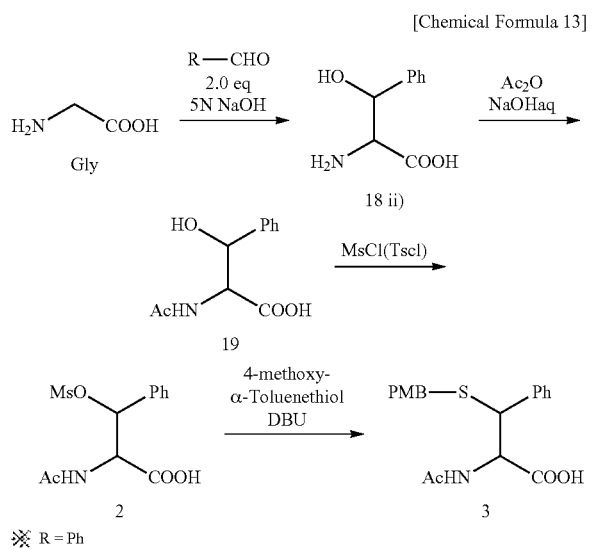

Synthesis Example 15

β-hydroxy-D,L-phenylalanine (Compound 18)

Glycine (7.0 g) was dissolved in 5 N NaOH (63.7 mL), and with chilling at 0° C., benzaldehyde (9.24 mL) was added in three portions every 10 minutes. This was then reacted at room temperature for 1 hour. This was subsequently acidified to pH 2-3 with 5 N HCl (93.2 mL), and then concentrated under reduced pressure at 60° C. To the crude product obtained was added methanol (120 mL) at room temperature. The salt insoluble to methanol (sodium chloride) was filtered, and the solution was concentrated under reduced pressure. This was then redissolved in methanol (100 mL), and recrystallized by allowing the pH to be 6-7 with triethylamine to obtain Compound 18 (7.0 g).

$C_9H_{11}NO_3$ [M+H]$^+$: Cal 182.07. Found 182.20.

Synthesis Example 16

N-Acetyl-β hydroxy-D,L-phenylalanine (Compound 19)

β-hydroxy-D,L-phenylalanine (3.0 g) was dissolved in 5 N sodium hydroxide aqueous solution (10 ml), and acetic anhydride (1.0 eq.) and 5 N sodium hydroxide aqueous solution (2 mL) were added in three portions every 15 minutes. This was lastly acidified to pH 2-3 with 5 N HCl, and then extracted three times with ethyl acetate. The organic layer was dried with magnesium sulfate, filtered, and concentrated under reduced pressure to obtain Compound 19 (1.0 g).

$C_{11}H_{13}NO_4$ [M+H]$^+$: Cal 224.08. Found 224.20.

Synthesis Example 17

N-Acetyl-β-O-mesyl-D,L-phenylalanine (Compound 2)

In the presence of argon, Compound 19 (15.0 mg) obtained by the method of Synthesis Example 16 was dissolved in acetonitrile (350 μL), triethylamine (14.6 μL) and mesyl chloride (6.5 μL) were added, and reacted at ordinary temperature for 2 hours. The compound produced by the reaction was extracted with ethyl acetate, and then washed with saturated ammonium chloride aqueous solution, water, and saturated saline. The organic layer was dried with magnesium sulfate, filtered, and concentrated under reduced pressure to obtain Compound 2. Confirmation that the compound obtained is Compound 2 having the hydroxyl group at the β-position mesylated was made by mass spectrometry.

$C_{12}H_{15}NO_6S$ [M+Na]$^+$: Cal 324.05. Found 324.1.

Synthesis Example 18

N-Acetyl-β-methoxybenzylmercapto-D,L-phenylalanine (Compound 3)

With a method similar to Synthesis Example 11, to a DMF solution of Compound 2 was added dropwise a DMF solution of a DBU salt of 4-methoxy-α-toluenethiol in the presence of argon at room temperature and reacted for 3 hours, and similarly extracted and washed to obtain Compound 3.

From the above Synthesis Example, a D,L-amino acid derivative possessing a protected thiol group at the β-position can be obtained by using glycine as the raw material to synthesize a β-hydroxy-amino acid derivative and introducing a protected thiol group at the β-position instead of the hydroxyl group at the β-position. Those skilled in the art will be able to synthesize D,L-amino acid derivatives of various structures not limited to aromatic amino acids possessing a protected thiol group at the β-position by this method by referring to the description herein. Optically active amino acid derivatives of various structures possessing a protected thiol group at the β-position can be efficiently obtained by a simple method by carrying out a method similar to Synthesis Example 7 on the D,L-amino acid derivative obtained.

Manufacture of a D-Amino Acid Derivative Possessing a Thiol Group at the β-Position As represented in the following reaction formula, the synthesis reaction of a D-amino acid derivative possessing a thiol group at the β-position was carried out with D-aminoacylase. Compound numbers indicated after compound names in Synthesis Examples indicate compound numbers indicated in the following reaction formula.

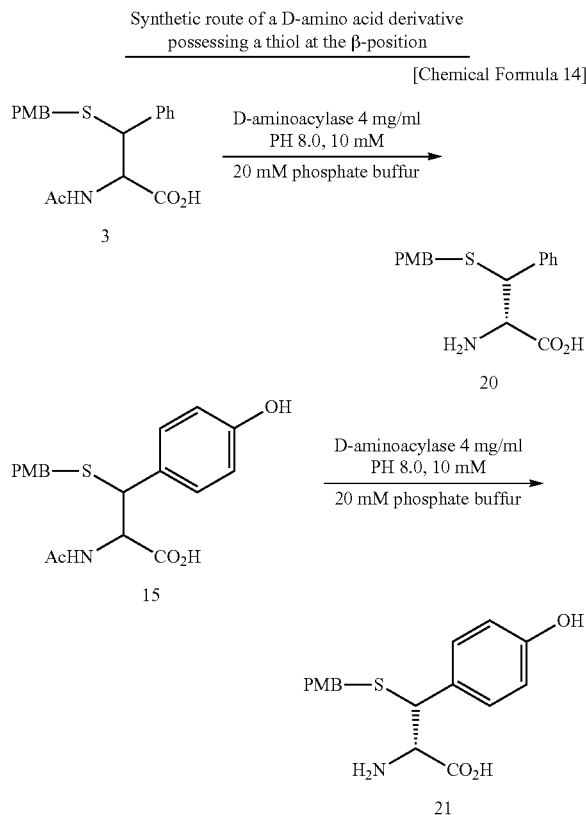

Synthesis Example 19

β-methoxybenzylmercapto-D-phenylalanine (20)

Compound 3 (1 mg, 28 μmol) was dissolved in phosphate buffer (pH 8.0, 140 μL), and then a separately prepared phosphate buffer solution (pH 8.0, 140 μL) of D-aminoacylase (from *E. coli*) (1 mg, 250 U/mg; product name D-aminoacylase "Amano" from Amano Enzyme Inc.) was added, and this was reacted at 37° C. for 2 weeks. Analysis by HPLC was carried out to confirm the production of Compound 20 having the α-position amino group unprotected. HPLC was carried out with a Cadenza C-18 (75×4.6 mm) column and an elution condition of 0.1% aqueous TFA solution:90% acetonitrile aqueous solution (containing 0.1% TFA)=80:20->30:70 (15 min), flow rate 1 mL/min.

$C_{17}H_{19}NO_3S$ [M+H]$^+$: Cal 318.11. Found 318.73.

In this Synthesis Example 19, after completion of the enzyme reaction, it is also possible to perform purification after carrying out the N-Boc protection similarly to (Synthesis Example 7-1).

Synthesis Example 20

β-methoxybenzylmercapto-D-tyrosine (21)

Compound 15 (1 mg, 27 μmol) was dissolved in phosphate buffer (pH 8.0, 170 μL), and then a separately prepared phosphate buffer solution (pH 8.0, 100 μL) of D-aminoacylase (from *E. coli*) (1 mg, 250 U/mg; product name D-aminoacylase "Amano" from Amano Enzyme Inc.) was added, and this was reacted at 37° C. for 3 days. Analysis by HPLC was carried out to confirm the production of Compound 21 having the α-position amino group unprotected. HPLC was carried out with a Cadenza C-18 (75×4.6 mm) column and an elution condition of 0.1% aqueous TFA solution:90% acetonitrile aqueous solution (containing 0.1% TFA)=80:20->0:100 (15 min), flow rate 1 mL/min.

$C_{17}H_{19}NO_4S$ [M+H]$^+$: Cal 334.10. Found 334.66.

In this Synthesis Example 20, after completion of the enzyme reaction, it is also possible to perform purification after carrying out the N-Boc protection similarly to (Synthesis Example 7-1).

From the above Synthesis Example, the D-form could be efficiently obtained by a simple method from a D,L-amino acid derivative possessing a protected thiol group at the β-position. In other words, according to the manufacturing method that uses conventional D- or L-form amino acids as the raw material, reactions employing a heating condition or strong basic or strong acidic conditions could not be employed so as not to produce stereoisomerization for the α asymmetric carbon atom, but according to the manufacturing method of the present invention, an easier manufacturing step with superior reaction efficiency that employs these extreme conditions could be employed. Those skilled in the art will be able to refer to the description herein and efficiently synthesize not only L-amino acids but also D-amino acids by the manufacturing method of the present invention. Moreover, as described in Synthesis Example 7, by collecting the D,L-amino acid derivative that was unhydrolyzed by a hydrolase selective for L-forms and similarly reacting it as the starting compound with a hydrolase selective for D-forms, D- and L-amino acids are simultaneously synthesized as a D,L-amino acid derivative, and both D- and L-forms can be efficiently obtained. In contrast, the same could be said when a hydrolase selective for D-forms was reacted first. This is useful in stably supplying the raw material of L-proteins that exist in vivo as well as D-proteins or racemic proteins which have increasing demand in recent years and enabling industrial production of these proteins.

Although examples of employing an aromatic amino acid or glycine as the raw material of β-thioracemic amino acid was shown in the present Examples, this does not intend to deny the use of other amino acid derivatives as the starting material in the manufacturing method of the present invention. Those skilled in the art will be able to implement the present invention based on the method described herein with various amino acid derivatives as the starting material.

The invention claimed is:
1. A method of manufacturing a non-natural D- or L-amino acid derivative possessing a protected or non-protected thiol group at the β-position, comprising the following steps of:

(I) carrying out the following reactions on an amino acid derivative to manufacture an amino acid derivative possessing a protected or non-protected thiol group at the β-position comprising D- and L-forms:
(A) introducing a protected or non-protected thiol group at the β carbon atom of said amino acid derivative, and
(B) converting the amino group bound to the α carbon atom of said amino acid derivative into a substituent to be the substrate for an aminohydrolase selective for D- or L-amino acids,
and
(II) reacting the amino acid derivative obtained in (I) with an aminohydrolase selective for either one of D- or L-amino acids, and subsequently separating the hydrolyzed D- or L-amino acid derivative.

2. The method according to claim 1, which is a method of manufacturing a non-natural D- or L-amino acid derivative possessing a protected or non-protected thiol group and substituent $R^1$ at the β-position, wherein $R^1$ refers to the substituent moiety bound to the β carbon atom among side chain substituents that configure amino acids, except when it is a hydrogen atom, and
said step (I) comprises the following step (P) before said reaction (A):
(P) manufacturing an amino acid derivative possessing substituent $R^1$ and a leaving group L on the β carbon atom, and
said reaction (A) is carried out simultaneously with a reaction of detaching said leaving group L from the β carbon atom of the amino acid derivative.

3. The method according to claim 2, wherein substituent $R^1$ is an aromatic substituent, and
said step (P) comprises the following step (P-1):
(P-1) introducing a leaving group L at the β carbon atom of an amino acid derivative possessing substituent $R^1$ on the β carbon atom.

4. The method according to claim 2, wherein said step (P) comprises the following step (P-2):
(P-2) reacting glycine with an aldehyde compound represented by $R^1CHO$.

5. The method according to claim 1, wherein said step (B) comprises converting the amino group bound to the α carbon atom of said amino acid derivative into an acylamino group, and
the hydrolase selective for D- or L-amino acids in said step (II) is a D- or L-aminoacylase.

6. The method according to claim 1, wherein the step of separating the hydrolyzed D- or L-amino acid derivative in said step (II) comprises
a step of introducing a lipophilic protecting group into the hydrolyzed D- or L-amino acid derivative, and is
a step of utilizing the difference in hydrophobicity produced by the presence or absence of the lipophilic protecting group to separate the D- or L-amino acid derivative having the lipophilic protecting group introduced.

7. The method according to claim 1, which is a method of manufacturing non-natural D-amino acid derivative, wherein
in said step (II) a hydrolase selective for D-amino acids is employed, and subsequently the hydrolyzed D-amino acid derivative is separated.

8. The method according to claim 1, which is a method of manufacturing non-natural L-amino acid derivative, wherein in said step (II) a hydrolase selective for L-amino acids is employed, and subsequently the hydrolyzed L-amino acid derivative is separated.

9. The method according to claim 1, wherein the thiol group introduced in said step (A) is a thiol group protected by a protecting group selected from a PMB (para-methoxybenzyl) group, an Acm (acetamidomethyl) group, a benzyl group, a Trt (trityl) group, a disulfide group, and a t-butyl group.

10. A method of manufacturing optically resolved non-natural D- and L-amino acid derivatives possessing a protected or non-protected thiol group at the β-position, comprising the following steps of:
(I) carrying out the following reactions on an amino acid derivative to manufacture an amino acid derivative possessing a protected or non-protected thiol group at the β-position comprising D- and L-forms:
(A) introducing a protected or non-protected thiol group at the β carbon atom of said amino acid derivative, and
(B) converting the amino group bound to the α carbon atom of said amino acid derivative into a substituent to be the substrate for an aminohydrolase selective for D- or L-amino acids,
(II) reacting the amino acid derivative obtained in (I) with an aminohydrolase selective for D-amino acids, and subsequently separating the hydrolyzed D-amino acid derivative,
and
(III) hydrolyzing the L-amino acid derivative that was not hydrolyzed in (II), and subsequently obtaining the hydrolyzed L-amino acid derivative.

11. A method of manufacturing optically resolved non-natural D- and L-amino acid derivatives possessing a protected or non-protected thiol group at the β-position, comprising the following steps of:
(I) carrying out the following reactions on an amino acid derivative to manufacture an amino acid derivative possessing a protected or non-protected thiol group at the β-position comprising D- and L-forms:
(A) introducing a protected or non-protected thiol group at the β carbon atom of said amino acid derivative, and
(B) converting the amino group bound to the α carbon atom of said amino acid derivative into a substituent to be the substrate for an aminohydrolase selective for D- or L-amino acids,
(II) reacting the amino acid derivative obtained in (I) with an aminohydrolase selective for L-amino acids, and subsequently separating the hydrolyzed L-amino acid derivative,
and
(III) hydrolyzing the D-amino acid derivative that was not hydrolyzed in (II), and subsequently obtaining the hydrolyzed D-amino acid derivative.

12. The method according to claim 1, wherein said step (B) comprises converting the amino group bound to the α carbon atom of said amino acid derivative into an acylamino group,
the amino acid derivative obtained in (I) described in step (II) is a composition comprising D- and L-forms for the α carbon atom represented by the following formula:

[Chemical Formula 1]

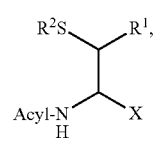

wherein $R^2$ represents a hydrogen atom or a protecting group for the thiol group, X represents a protected or non-protected carboxyl group, Acyl indicates an acyl group, and $R^1$ indicates the substituent moiety bound to the β carbon atom among side chain substituents that configure amino acids, except when it is a hydrogen atom, and the hydrolase selective for D- or L-amino acids in said step (II) is a D- or L-aminoacylase.

13. The method according to claim 1, wherein an amino acid derivative comprising D- and L-forms for the α carbon atom or an amino acid derivative in which the α carbon atom is not an asymmetric carbon atom is employed as the raw material.

14. The method according to claim 11, wherein the amino acid comprises D- and L-forms for the α carbon atom or the amino acid comprises an α carbon atom that is not an asymmetric carbon atom.

* * * * *